(12) United States Patent
Fouz et al.

(10) Patent No.: US 10,982,266 B2
(45) Date of Patent: Apr. 20, 2021

(54) NUCLEIC ACID-POLYMER CONJUGATES FOR BRIGHT FLUORESCENT TAGS

(71) Applicant: CARNEGIE MELLON UNIVERSITY, Pittsburgh, PA (US)

(72) Inventors: Munira F. Fouz, Gaithersburg, MD (US); Krzysztof Matyjaszewski, Pittsburgh, PA (US); Bruce A. Armitage, Pittsburgh, PA (US); Subha Ranjan Das, Pittsburgh, PA (US); Saadyah Averick, Pittsburgh, PA (US)

(73) Assignee: CARNEGIE MELLON UNIVERSITY, Pittsburgh, PA (US)

( * ) Notice: Subject to any disclaimer, the term of this patent is extended or adjusted under 35 U.S.C. 154(b) by 483 days.

(21) Appl. No.: 15/802,066

(22) Filed: Nov. 2, 2017

(65) Prior Publication Data

US 2018/0142288 A1 May 24, 2018

Related U.S. Application Data

(60) Provisional application No. 62/496,954, filed on Nov. 3, 2016.

(51) Int. Cl.
| | |
|---|---|
| *C12Q 1/68* | (2018.01) |
| *C12Q 1/6834* | (2018.01) |
| *C07H 21/04* | (2006.01) |
| *C08L 57/00* | (2006.01) |
| *G01N 33/58* | (2006.01) |
| *C08L 57/12* | (2006.01) |
| *A61K 47/68* | (2017.01) |

(52) U.S. Cl.
CPC .......... *C12Q 1/6834* (2013.01); *C07H 21/04* (2013.01); *C08L 57/00* (2013.01); *C08L 57/12* (2013.01); *G01N 33/582* (2013.01); *A61K 47/6883* (2017.08); *C08F 2438/01* (2013.01); *C08L 2203/02* (2013.01); *C08L 2205/14* (2013.01)

(58) Field of Classification Search
USPC ......... 435/6.1, 6.11, 91.1, 183; 436/94, 501; 536/23.1, 24.3
See application file for complete search history.

(56) References Cited

U.S. PATENT DOCUMENTS

| | | |
|---|---|---|
| 5,763,546 A | 6/1998 | Jung |
| 5,789,487 A | 8/1998 | Matyjaszewski |
| (Continued) | | |

OTHER PUBLICATIONS

Lee et al., Signal-Amplifying Conjugated Polymer-DNA Hybrid Chips. Angew. Chem. Int. Ed., 46, 4667-4670. 2007.*

(Continued)

*Primary Examiner* — Frank W Lu
(74) *Attorney, Agent, or Firm* — Bartony & Associates LLC

(57) ABSTRACT

A composition includes a polymer including extending chains, side chains, or branches. One (or more) of a plurality of a first strand of nucleic acid is attached to each of a plurality of the side chains. One (or more) of a plurality of a second strand of nucleic acid, which is complementary to the first strand of nucleic acid, is complexed to each of the plurality of the first strand of nucleic acid to form a double strand of nucleic acid on each of the plurality of the side chains. At least one fluorescent compound is associated with the double strand of nucleic acid on each of the plurality of the side chains.

18 Claims, 12 Drawing Sheets

Specification includes a Sequence Listing.

(56) References Cited

U.S. PATENT DOCUMENTS

| | | | |
|---|---|---|---|
| 5,807,937 | A | 9/1998 | Matyjaszewski |
| 5,945,491 | A | 8/1999 | Matyjaszewski |
| 6,054,272 | A | 4/2000 | Glazer |
| 6,111,022 | A | 8/2000 | Matyjaszewski |
| 6,121,371 | A | 9/2000 | Matyjaszewski |
| 6,124,411 | A | 9/2000 | Matyjaszewski |
| 6,162,882 | A | 12/2000 | Matyjaszewski |
| 6,407,187 | B1 | 6/2002 | Matyjaszewski |
| 6,512,060 | B1 | 1/2003 | Matyjaszewski |
| 6,538,091 | B1 | 3/2003 | Matyjaszewski |
| 6,541,580 | B1 | 4/2003 | Matyjaszewski |
| 6,624,262 | B2 | 9/2003 | Matyjaszewski |
| 6,627,314 | B2 | 9/2003 | Matyjaszewski |
| 6,759,491 | B2 | 7/2004 | Matyjaszewski |
| 6,790,919 | B2 | 9/2004 | Matyjaszewski |
| 6,887,962 | B2 | 5/2005 | Matyjaszewski |
| 7,019,082 | B2 | 3/2006 | Matyjaszewski |
| 7,049,373 | B2 | 5/2006 | Matyjaszewski |
| 7,064,166 | B2 | 6/2006 | Matyjaszewski |
| 7,125,938 | B2 | 10/2006 | Matyjaszewski |
| 7,157,530 | B2 | 1/2007 | Matyjaszewski |
| 7,332,550 | B2 | 2/2008 | Matyjaszewski |
| 7,407,995 | B2 | 8/2008 | Ok |
| 7,572,874 | B2 | 8/2009 | Matyjaszewski |
| 7,678,869 | B2 | 3/2010 | Matyjaszewski |
| 7,795,355 | B2 | 9/2010 | Matyjaszewski |
| 7,825,199 | B1 | 11/2010 | Matyjaszewski |
| 7,893,173 | B2 | 2/2011 | Matyjaszewski |
| 7,893,174 | B2 | 2/2011 | Matyjaszewski |
| 8,252,880 | B2 | 8/2012 | Matyjaszewski |
| 8,273,823 | B2 | 9/2012 | Matyjaszewski |
| 8,349,410 | B2 | 1/2013 | Huang |
| 8,367,051 | B2 | 2/2013 | Matyjaszewski |
| 8,404,788 | B2 | 3/2013 | Matyjaszewski |
| 8,445,610 | B2 | 5/2013 | Kwak |
| 8,816,001 | B2 | 8/2014 | Mehl |
| 8,865,795 | B1 | 10/2014 | Xin |
| 8,871,831 | B2 | 10/2014 | Huang |
| 8,962,764 | B2 | 2/2015 | Matyjaszewski |
| 9,243,274 | B2 | 1/2016 | Mehl |
| 9,410,020 | B2 | 8/2016 | Matyjaszewski |
| 9,533,297 | B2 | 1/2017 | Matyjaszewski |
| 2007/0281294 | A1* | 12/2007 | Schorling ............. C12Q 1/701 435/5 |
| 2014/0183055 | A1 | 7/2014 | Matyjaszewski |
| 2014/0275420 | A1 | 9/2014 | Matyjaszewski |
| 2017/0058329 | A1 | 3/2017 | Chilkoti |

OTHER PUBLICATIONS

Fouz et al., Bright Fluorescent Nanotags from Bottlebrush Polymers with DNA-Tipped Bristles. ACS Cent. Sci., 1, 431-438, published online on Jun. 29, 2015.*

Chen et al., DNA-Grafted Polypeptide Molecular Bottlebrush Prepared via Ring-Opening Polymerization and Click Chemistry. Macromolecules, 45, 9579-9584, 2012.*

Huang et al., Thermodynamically modulated partially double-stranded linear DNA probe design for homogeneous real-time PCR. Nucleic Acids Research, 35, e101, 2007.*

Matyjaszewski, Krzysztof, Comparison and Classification of Controlled/Living Radical Polymerizations,;ACS Symposium Series; American Chemical Society, 2000, pp. 1-26.

Kickelbick, Guido et al., The Cooper Catalyst in Atom transfer radical Polymerizations: Structural Observations; ACS Symposium Series; American Chemical Society,2000, pp. 211-222.

Ogawa, Mikako et al., H-Type Dimer Formation of Fluorophores: A Mechanism for Activatable, in vivo Optical Molecular Imaging; ACS Chemical Biology. vol. 4, No. 7, 2009—pp. 535-546.

Ozhalici-Unal, Hayriye et al., Fluorescent DNA Nanotags Based on a Self-Assembled DNA Tetrahedron; ACS Nano, vol. 3, No. 2, 2009, pp. 425-433.

Gong, Haibiao et al., A Homogeneous Fluorescence-based method to Measure Antibody Internalization in Tumor Cells; Analytical Biochemestry; 469, 2015, pp. 1-3.

Bandura, Dmitry R. et al., Mass Cytometry: Technique for Real Time Single Cell Multitarget Immunoassay Based on Inductively Coupled Plasma Time-of-Flight Mass Spectrometry; Anal. Chem. 2009; 81; pp. 6813-6822.

Kwak, Minseok et al., Nucleic Acid/Organic Polymer hybrid Materials: Synthesis, Superstructures and Applications; Angew. Chem. int. Ed. 2010, 49, pp. 8574-8587.

Lefevre, Charles et al., Texas red-X and Rhodamine Red-X, New Derivatives of Sulforhodamine 101 and Lissamine Rhodamine B with Improved Labeling and Fluorescence Properties; Bioconjugate Chem. 1996; 7; pp. 482-489.

Siiman, Olavi et al., Fluorescent Neoglycoproteins: Antibody-Aminodextran-Phycobiliprotein Conjugates; Bioconjugate Chem. 1999; 10; pp. 1090-1106.

Stadler, Andrea L. et al., FLuorescent DNA Nanotags, Featuring Covalently Attached Intercalating Dyes; Synthesis, Antibody Conjugation, and Intracellular Imaging; Bioconjugate Chem. 2011; 22; pp. 1491-1502.

Paredes, Eduardo et al., Optimization of Acetonitrile co-solvent and Cooper Stroichiometry for Pseudo-Ligandless Click Chemistry with Nucleic Acids; Bioorganic & Medical Chemistry Letters; 22; 2012; pp. 5313-5316.

Lesaicherre, Marie-Laure et al., Antibody-Based Fluorescence Determination of Kinase Activity on Peptide Array; Bioorganic & Medical Chemistry Letters; 12; 2002; pp. 2085-2088.

Ouellet, Jonathan et al., Orientation of Cyanine Fluorophores Terminally Attached to DNA via long, Flexible Tethers; Biophysical Journal; vol. 101; 2011; pp. 1148-1154.

Ohya, Tomoshi et al., Improved Production of Recombinant Human Antithrombin III in Chinese Hamster Ovary Cells by ATF4 Overexpression; Biotechnology and Bioengineering, vol. 100; No. 2; 2008, pp. 317-324.

Lobbestael, Evy et al., Immunohistochemical Detection of Transgone Expression in the Brain Using Small Epitope Tags; Biotechnology; 2010; pp. 1-10.

Kherlopian, Armen R. et al., A Review of Imaging Techniques for Systems Biology; BMC Systems Biology; 2008, pp. 1-18.

Bobrow, Mark et al., Tyramide Signal Amplification (TSA) Systems for the Enhancement of ISH Signals in Cytogenetics; Current Protocols in Cytometry; 2000; Unit 8.9, pp. 1-16.

Jiang, Hui et al., Biomolecule-Functionalized Prolymer Brushes; Chem. Soc. Rev.; 2013; 42; pp. 3394-3426.

Clutter, Matthew R., et al., Tyramide Signal Amplification for Analysis of Kinase Activity by Intracellular Flow Cytometry; Cytometry A.;77(11); Nov. 2010; pp. 1020-1031.

Lichtman, Jeff W. et al., Fluorescence Microscopy; Nature Methods; vol. 2; No. 12; 2005; pp. 910-919.

Yan, Xiaomci et al., On the Development of a Microsphere-Based Multiplexed Immunoassay for Influenza Virus Typing and Subtyping by Flow Cytometry; International Congress Series 1263; 2004; pp. 342-345.

Liu, Kai et al., Nucleic Acid Chemistry in the Organic Phase: From Functionalized Oligonucleotides to DNA Side Chain Polymers; J. Am.Chem. Soc.; 136; 2014; pp. 14255-14262.

Benvin, Andrea L. et al., Fluorescent DNA Nanotags: Supramolecular Fluorescent Labels Based on Intercalating Dye Arrays Assembled on Nanostructured DNA Templates; J. Am.Chem. Soc.; 129; 2007; pp. 2025-2034.

Johnson, Jeremiah A. et al.; Core-Clickable PRG-Branch-Azide Bivalent-Bottle-Brush Polymers by ROMP: Grafting-Through and Clicking-To; J. Am.Chem. Soc.; 133; 2011; pp. 559-566.

Averick, Saadyah E. et al.; Autotransfecting Short Interfering RNA Through Facile Covalent Polymer Escorts; J. Am.Chem. Soc.135; 2013; pp. 12508-12511.

Bracha, Dan et al., Dendritic and Nanowire Assemblies of Condensed DNA Polymer Brushes; J. Am.Chem. Soc.; 136; 2014; pp. 4945-1953.

Matyjaszewski, Krzysztof et al., Macromolecular Engineering by Atom transfer radical Polymerization; Am. Chem. Soc.; 136; 2014; pp. 6513-6533.

(56) References Cited

OTHER PUBLICATIONS

Averick, Saadyah et al., Well_Defined Biohybrids using Reversible-Deactivation radical Polymerization Procedures; Journal of Controlled Release; 205;2015; pp. 45-57.

Speel, Ernst J. M. et al., Amplification Methods to Increase the Sensitivity of In Situ Hybridization: Play CARD(S); The journal of Histochemistry & Cytochemistry; vol. 47(3); 1999; pp. 281-288.

Mayer, Gaetan et al., Immunogold Signal Amplification: Application of the CARD Approach to Electron Microscopy; The journal of Histochemistry & Cytochemistry; vol. 47(4); 1999; pp. 421-429.

Wang, Ningshan et al., Novel Immunohistochemical Techniques Using Discrete Signal Amplification Systems for Human Cutaneous Peripheral Nerve Fiber Imaging; The journal of Histochemistry & Cytochemistry; vol. 59(4); 2011; pp. 382-390.

Karkmann, Ulrich et al., Enzymatic signal amplification for sensitive detection of intracellular antigens by flow cytometry; Journal of Immunological Methods ; 230; 1999.; pp. 113-120.

Dasso, Joseph et al., A comparison of ELISA and flow microsphere-based assays for quantification of immunoglobulins; Journal of Immunological Methods; 263; (2002); pp. 23-33.

Yan, Xiaomei et al., Microsphere-based duplexed immunoassay for influenza virus typing by flow cytometry; Journal of Immunological Methods 284 (2004) 27-38.

Korb, Melissa L. et al., Use of monoclonal antibody—IRDye800CW bioconjugates in the resection of breast cancer; Journal of Surgical Reasearch; 188; 2014; pp. 119-128.

Rosen, Christian B. et al, Template-directed covalent conjugation of DNA to native antibodies, transferrin and other metal-binding proteins; Nature Chemistry; vol. 6; Sep. 2014; 804-809.

Giesen, Charlotte et al., Highly multiplexed imaging of tumor tissues with subcellular resolution by mass cytometry; Nature Methods; vol. 11, No. 4; Apr. 2014, 417-425.

Bernardes, Goncalo J. L. et al; Site-specific chemical modification of antibody fragments using traceless cleavable linkers; Nature Protocols, vol. 8; No. 11; 2013; pp. 2079-2088.

Evanko, Daniel; Focus on fluorescence imaging Principles and practice of microscope techniques; Nature Methods; vol. 2; No. 12, Dec. 2005, p. 901.

Flors, Cristina; Photoswitching of monomeric and dimeric DNA-intercalating cyanine dyes for super-resolution microscopy applications; Photochem. Photobiol. Sci., 2010, 9, 643-648.

Sheiko, Sergei S., et al; Cylindrical molecular brushes: Synthesis, characterization, and properties; Progress in Polymer Science 33 (2008) 759-785.

Lee, Hyung-Il et al., Stimuli-responsive molecular brushes; Progress in Polymer Science 35 (2010) 24-44.

Bendall, Sean C., et al; Single-Cell Mass Cytometry of Differential Immune and Drug Responses Across a Human Hematopoietic Continuum; Science; vol. 332; May 6, 2011, pp. 687-696.

Barbey, Raphael et al., Polymer Brushes via Surface-Initiated Controlled Radical Polymerization: Synthesis, Characterization, Properties and Applications; Chemical Reviews, 2009, vol. 109, No. 11, pp. 5437-5527.

\* cited by examiner

YOYO-1

Hexynyl-A - 5'-Hexynyl- GCA CT GCA GTT GGA TCC CAT AGC -3' (23 mer)

Fig. 1F

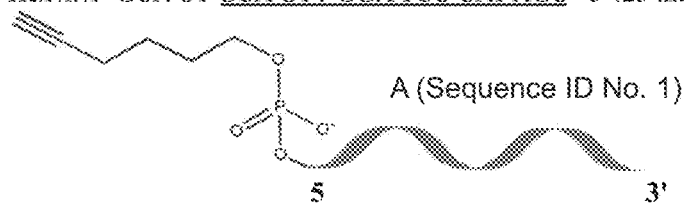

A (Sequence ID No. 1)

Hexynyl-B - 5'-Hexynyl-GCT AT CCA TCA GAA TTC GCG ACG -3' (23 mer) - completely complementary to Seq.B'

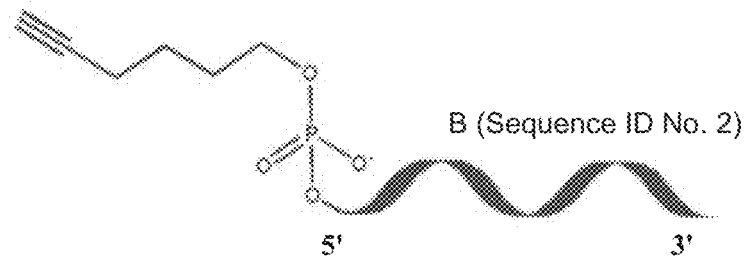

B (Sequence ID No. 2)

A$_{comp}$ - 5'-ATC GA GCT ATG GGA TCC AAC TGC -3' (23 mer) (IDT)

A$_{comp}$ (Sequence ID No. 3)

Cy5 -A$_{comp}$ - 5'-Cy5- ATC GA GCT ATG GGA TCC AAC TGC -3' (23 mer)

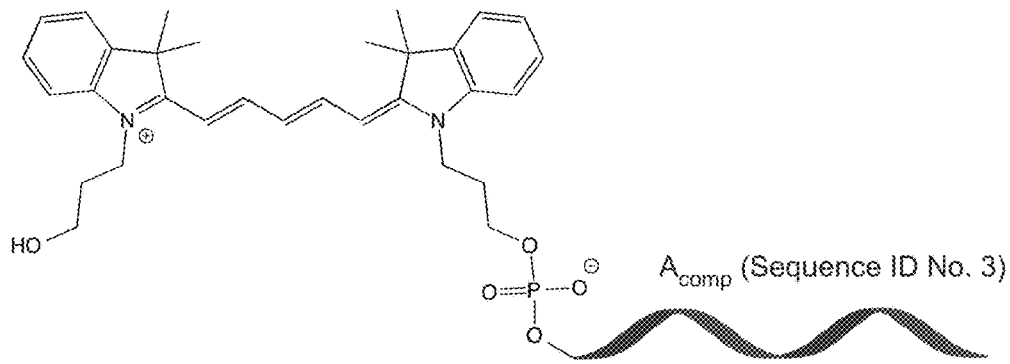

A$_{comp}$ (Sequence ID No. 3)

NH$_2$-A'- 5'-NH$_2$-GCT ATG GGA TCC AAC TGC AGT GC -3' (23 mer) (IDT) - completely complementary to Seq.A

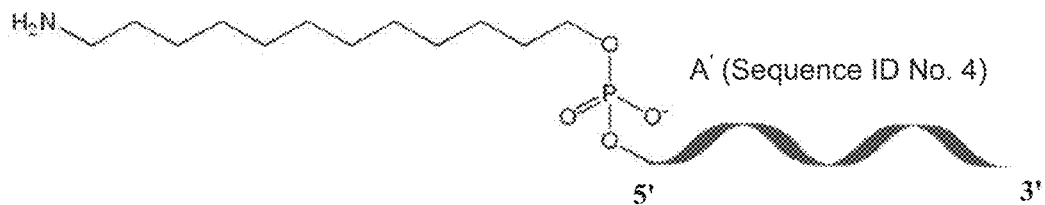

A' (Sequence ID No. 4)

NH$_2$-B' - 5'-NH$_2$-ATCGA CGT CGC GAA TTC TGA TGG ATA GC-3' (IDT) - completely complementary to Seq. B

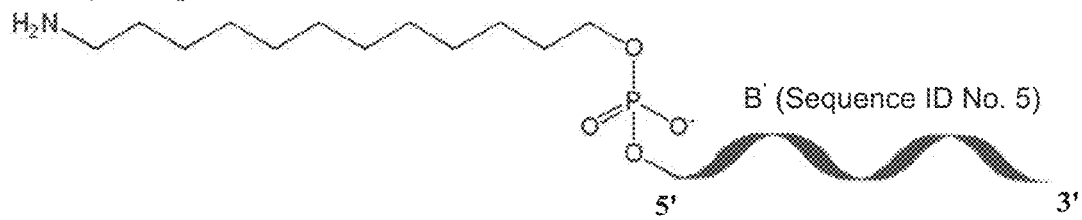

B' (Sequence ID No. 5)

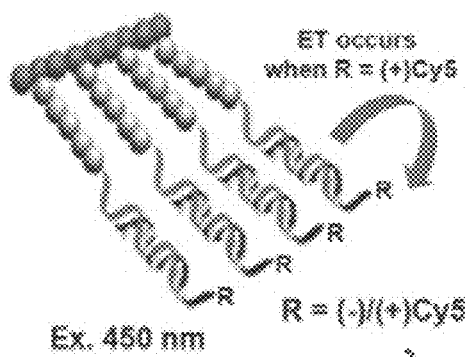
Fig. 2A
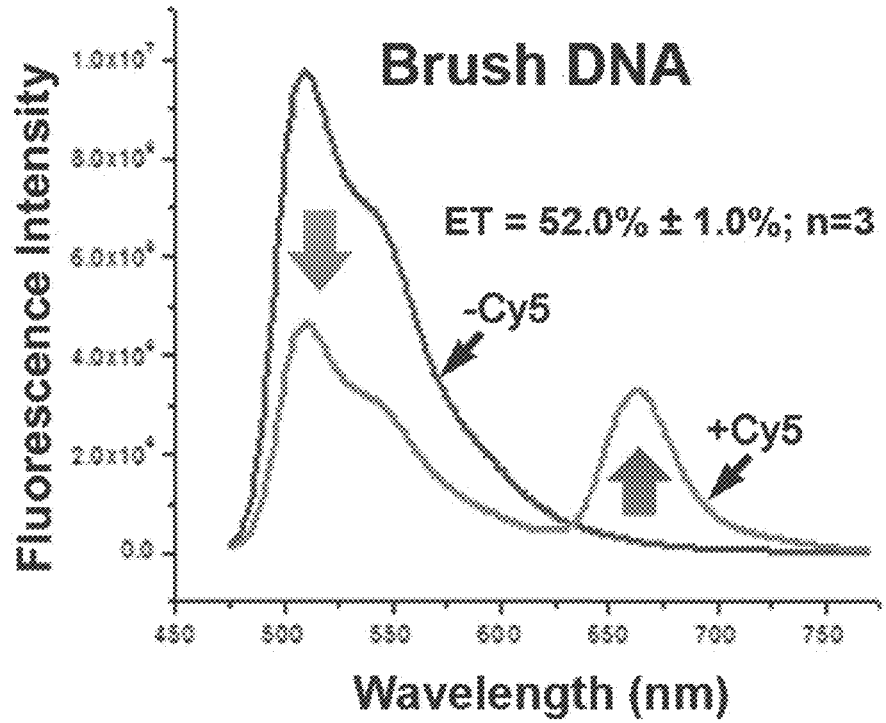
Fig. 2B
Fig. 2C

Yeast cell with the c-myc protein tagged to scFv

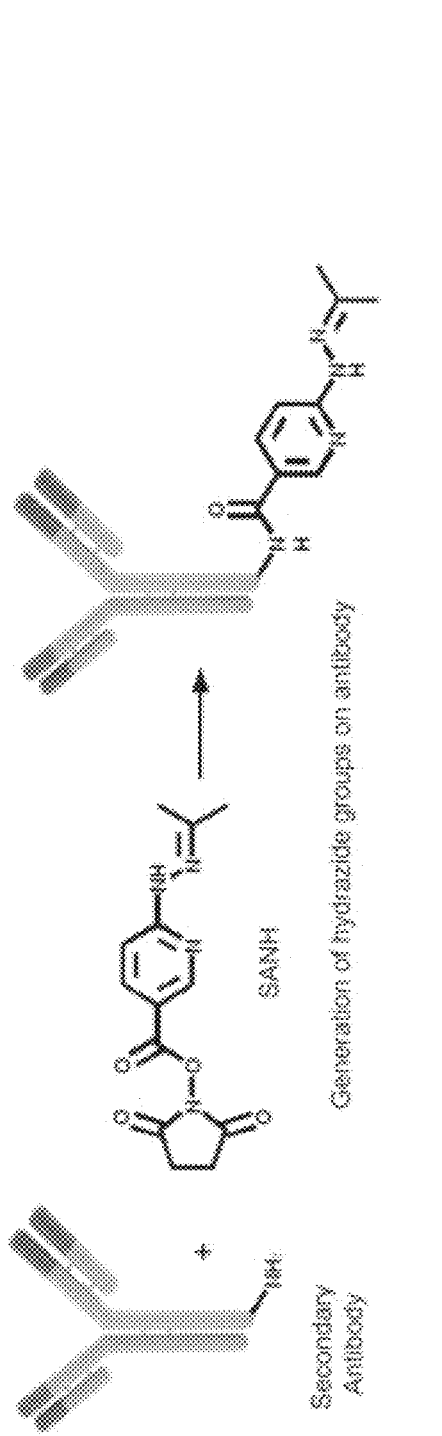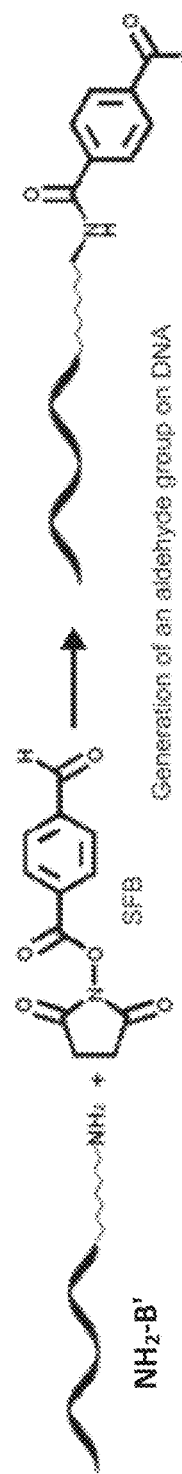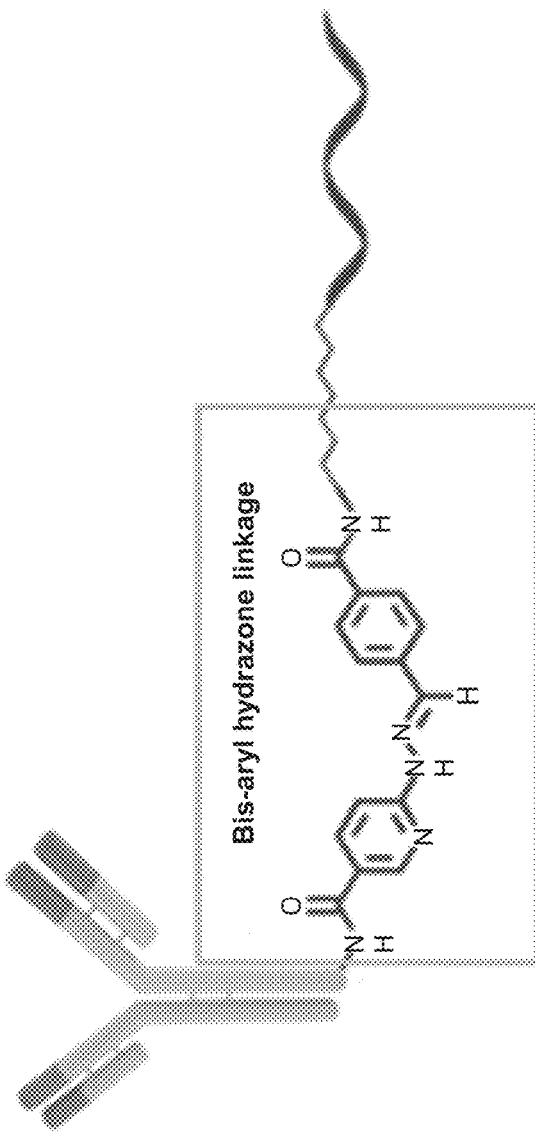
Fig. 5A
Fig. 5B
Fig. 5C

SEQUENCE LISTING

```
<160> NUMBER OF SEQ ID NOS: 5

<210> SEQ ID NO 1
<211> LENGTH: 23
<212> TYPE: DNA
<213> ORGANISM: Artificial Sequence
<220> FEATURE:
<223> OTHER INFORMATION: Synthetic construct

<400> SEQUENCE: 1
gcactgcagt tggatcccat agc                                             23

<210> SEQ ID NO 2
<211> LENGTH: 23
<212> TYPE: DNA
<213> ORGANISM: Artificial Sequence
<220> FEATURE:
<223> OTHER INFORMATION: Synthetic Construct

<400> SEQUENCE: 2
gctatccatc agaattcgcg acg                                             23

<210> SEQ ID NO 3
<211> LENGTH: 23
<212> TYPE: DNA
<213> ORGANISM: Artificial Sequence
<220> FEATURE:
<223> OTHER INFORMATION: Synthetic Construct

<400> SEQUENCE: 3
atcgagctat gggatccaac tgc                                             23
```

```
<210> SEQ ID NO 4
<211> LENGTH: 23
<212> TYPE: DNA
<213> ORGANISM: Artificial Sequence
<220> FEATURE:
<223> OTHER INFORMATION: Synthetic Construct

<400> SEQUENCE: 4
gctatgggat ccaactgcag tgc                                          23

<210> SEQ ID NO 5
<211> LENGTH: 28
<212> TYPE: DNA
<213> ORGANISM: Artificial Sequence
<220> FEATURE:
<223> OTHER INFORMATION: Synthetic construct

<400> SEQUENCE: 5
atcgacgtcg cgaattctga tggatagc                                     28
```

NUCLEIC ACID-POLYMER CONJUGATES FOR BRIGHT FLUORESCENT TAGS

CROSS-REFERENCE TO RELATED APPLICATIONS

This application claims benefit of U.S. Provisional Patent Application Ser. No. 62/496,954, filed Nov. 3, 2016, the disclosure of which is incorporated herein by reference.

GOVERNMENTAL INTEREST

This invention was made with government support under National Science Foundation Award No. 1501324. The government has certain rights in this invention.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Virtually every imaginable aspect of biological systems has succumbed to labeling through fluorescent probes that have been developed over the years. Fluorescent dyes coupled to affinity binders such as antibodies are common reporters in fluorescence microscopy, flow cytometry and microplate assays as well as in protein and nucleic acid blots. Despite the advent of competing approaches such as recombinant peptide tagging and mass spectrometry, antibody based detection remains the most broadly applicable means of localizing and quantitating specific components in a complex sample. Labeled secondary antibodies make stable and specific complexes with unlabeled primary antibodies, providing the foundation for most immunofluorescence protocols.

The number of target molecules per surface area or volume unit is a key variable in biological detection applications. To detect functionally important proteins with a natural low expression level, there remains a need to enhance the detectable signal The most straightforward way to enhance fluorescence signals is to increase the number of fluorophores available for detection. However increased labeling of proteins can lead to precipitation of the protein.

As an alternative, signal amplification methods can be used to get brighter signals. In catalytic reporter deposition (CARD) methods, the high turnover rate of enzymes like horseradish peroxidase and alkaline phosphatase generate high density labeling of a target protein or nucleic acid in situ. Hence in both immunohistochemical and immunoassay applications, careful control of timing is an essential prerequisite to obtain quantitative and re-producible results.

To avoid these potential limitations of amplification methods, an alternative is to increase the number of labels directly on affinity binders. A typical IgG antibody molecule has about ninety lysine residues, of which at most thirty can be modified under forcing conditions. However, maintenance of functional properties typically requires a degree of labeling of less than ten dyes per IgG, representing a low fraction of modification with individual fluorescent dyes. Antibodies labeled with more than four to six fluorophores per protein can exhibit reduced specificity and binding affinity. With higher degrees of substitution, the fluorescence obtained per added fluorophore is typically much lower than expected or calculated, due to self-quenching.

The use of soluble and relatively stable fluorescent proteins such as the phycobiliproteins, conjugated to antibodies could overcome the limitations arising from the high loading of low molecular weight dyes. On a molar basis, the fluorescence yield of a phycobiliprotein is equivalent to at least 30 unquenched fluorescein or 100 rhodamine molecules at comparable wavelengths. Further, fluorescent polystyrene microspheres heavily loaded with fluorescent dyes have been used as immuno-fluorescent reagents to deliver strong signals.

However, all current labeling schemes for fluorescent dyes suffer from one or more significant drawbacks. It remains desirable to provide straightforward and readily usable compositions, systems and methods for providing bright signals in fluorescent detection systems.

SUMMARY

In one aspect, a composition includes a polymer including extending chains, side chains, or branches. One (or more) of a plurality of a first strand of nucleic acid is attached to each of a plurality of the side chains. One of a plurality of a second strand of nucleic acid, which is complementary (that is, partially of full complementary) to the first strand of nucleic acid, is complexed to each of the plurality of the first strand of nucleic acid to form a double strand of nucleic acid on each of the plurality of the side chains. At least one fluorescent compound is associated with the double strand of nucleic acid on each of the plurality of the side chains.

In a number of embodiments, the composition further includes a moiety which has a binding affinity for one or more target species attached to one of the side chains. The one of the side chains to which the moiety is attached may, for example, include a third strand of nucleic acid. The moiety may, for example, be attached to a fourth strand of nucleic acid which is complementary to the third strand of nucleic acid, wherein the fourth strand of nucleic acid is complexed to the third strand of nucleic acid. The moiety may also be attached to one of the first strands of nucleic acid via complexing thereto of a strand of nucleic acid, which is complementary to the first strand of nucleic acid, and which is attached to the moiety. Alternatively, the moiety may be covalently attached to the one of the side chains of the polymer. In a number of embodiments, the moiety is a protein such as an antibody. The moiety may, for example, also be a peptide (including a cyclic peptide), an aptamer (that is, an oligonucleotide or peptide molecule that binds to a specific target molecule), a glycoside, or a glycopeptides.

In a number of embodiments, the polymer is a bottlebrush copolymer including a backbone from which the side chains extend. The side chains may, for example, be formed via a reversible-deactivation radical polymerization such an atom transfer radical polymerization.

The at least one fluorescent compound may, for example, be associated with the double strand of nucleic acid via intercalation with the double strands of nucleic acid. A plurality of fluorescent compounds may, for example, be intercalated with the double strands of nucleic acid. In a number of embodiments, each of the double strands of nucleic acid further includes at least one fluorescent compound different from the plurality of fluorescent compounds to effect energy transfer. In a number of embodiments, excitation energy can be transferred between different fluorescent compounds (that is, acceptor/donor combinations) to effect a red shift in an emission wavelength. In a number of embodiment, the at least one fluorescent compound different from the plurality of fluorescent compounds is covalently attached to the second strand of nucleic acid.

In a number of embodiments, the at least one fluorescent compound is covalently attached to the second strand of nucleic acid. A plurality of fluorescent compounds are attached to the second strand of nucleic acid. One or more of the same or different fluorescent compounds may be attached to the first strand of nucleic acid and/or to the second strand of nucleic acid. Covalently bound fluorescent compounds may be chosen to effect energy transfer. In a number of embodiments, the second strand of nucleic acid is complementary to a portion of the first strand of nucleic acid, and the composition further includes a fifth strand of nucleic acid which is complementary to another or second portion of the first strand of nucleic acid. A plurality of fluorescent compounds may, for example, be attached to at least one of the second strand of nucleic acid or the fifth strand of nucleic acid. The polymer may, for example, be a bottlebrush copolymer including a backbone from which the side chains extend. As described above, such side chains may, for example, be formed via a reversible-deactivation radical polymerization such as atom transfer radical polymerization.

In a number of embodiments, the first strand of nucleic acid is a first strand of DNA and the second strand of nucleic acid is a second strand of DNA.

In another aspect, a method of labeling a target species includes attaching a label to the target species which includes a composition as described above. In that regard, the composition includes a polymer having side chains. One (or more) of a plurality of a first strand of nucleic acid is attached to each of a plurality of the side chains. One of a plurality of a second strand of nucleic acid, which is complementary to the first strand of nucleic acid, is complexed to each of the plurality of the first strand of nucleic acid to form a double strand of nucleic acid on each of the plurality of the side chains. At least one fluorescent compound is associated with the double strand of nucleic acid on each of the plurality of the side chains.

As described above, the composition may further include a moiety which has a binding affinity for one or more target species attached to one of the side chains. The one of the side chains to which the moiety is attached may, for example, include a third strand of nucleic acid. The moiety may, for example, be attached to a fourth strand of nucleic acid which is complementary to the third strand of nucleic acid, wherein the fourth strand of nucleic acid is complexed to the third strand of nucleic acid. The moiety may also be attached to one of the first strands of nucleic acid via complexing thereto of a strand of nucleic acid, which is complementary to the first strand of nucleic acid, and which is attached to the moiety. Alternatively, the moiety may be covalently attached to the one of the side chains of the polymer. In a number of embodiments, the moiety is a protein such as an antibody. In a number of embodiments, the antibody is a secondary antibody. The secondary antibody may, for example, have affinity for a primary antibody, and the primary antibody has affinity for the target species. The label may, for example, include the secondary antibody and the primary antibody. The moiety may, for example, also be a peptide (including a cyclic peptide), an aptamer (that is, an oligonucleotide or peptide molecule that binds to a specific target molecule), a glycoside, or a glycopeptides.

As also described above, the polymer may, for example, be a bottlebrush copolymer including a backbone from which the side chains extend. The side chains may, for example, be formed via a reversible-deactivation radical polymerization such an atom transfer radical polymerization.

The at least one fluorescent compound may, for example, be associated with the double strand of nucleic acid via intercalation with the double strands of nucleic acid. A plurality of fluorescent compounds may, for example, be intercalated with the double strands of nucleic acid. In a number of embodiments, each of the double strands of nucleic acid further includes at least one fluorescent compound different from the plurality of fluorescent compounds to effect energy transfer. In a number of embodiments, excitation energy can be transferred between different fluorescent compounds (that is, acceptor/donor combinations) to effect a red shift in an emission wavelength. In a number of embodiment, the at least one fluorescent compound different from the plurality of fluorescent compounds is covalently attached to the second strand of nucleic acid.

In a number of embodiments, the at least one fluorescent compound is covalently attached to the second strand of nucleic acid. A plurality of fluorescent compounds are attached to the second strand of nucleic acid. One or more of the same or different fluorescent compounds may be attached to the first strand of nucleic acid and/or to the second strand of nucleic acid. Covalently bound fluorescent compounds may be chosen to effect energy transfer. In a number of embodiments, the second strand of nucleic acid is complementary to a portion of the first strand of nucleic acid, and the composition further includes a fifth strand of nucleic acid which is complementary to another or second portion of the first strand of nucleic acid. A plurality of fluorescent compounds may, for example, be attached to at least one of the second strand of nucleic acid or the fifth strand of nucleic acid. The polymer may, for example, be a bottlebrush copolymer including a backbone from which the side chains extend. As described above, such side chains may, for example, be formed via a reversible-deactivation radical polymerization such as atom transfer radical polymerization.

In a number of embodiments, the first strand of nucleic acid is a first strand of DNA and the second strand of nucleic acid is a second strand of DNA.

In a further aspect, a method of forming a mobile fluorescent label include forming a polymer scaffold having side chains, attaching one of a plurality of a first strand of nucleic acid to each of a plurality of the side chains, complexing one of a plurality of a second strand of nucleic acid which, is complementary to the first strand of nucleic acid, to each of the plurality of the first strand of nucleic acid to form a double strand of nucleic acid on each of the plurality of the side chains, wherein at least one fluorescent compound is associated with the double strand of nucleic acid on each of the plurality of the side chains. The mobile fluorescent label may be further characterized as described above.

The present systems, methods and compositions, along with the attributes and attendant advantages thereof, will best be appreciated and understood in view of the following detailed description taken in conjunction with the accompanying drawings.

BRIEF DESCRIPTION OF THE DRAWINGS

FIG. 1F illustrates representative synthetic DNA sequences and linking groups used in representative studies hereof.

FIG. 2A illustrates schematically wavelength shifting via Energy Transfer (ET) from intercalated YOYO-1 to terminal Cy5 dyes (terminal spheres) on each complementary strand of DNA, which provides for emission at a higher wavelength.

FIG. 2B illustrates a fluorescence intensity spectra from DNA attached to a bottlebrush polymer hereof (Brush DNA) wherein the traces correspond to signals from brush DNAs that include (+Cy5) or exclude (−Cy5) covalently attached terminal Cy5 on all the hybridized DNA strands.

FIG. 2C illustrates a fluorescence intensity spectra for DNA in solution (Non-brush DNA) wherein the traces correspond to signals from the Non-brush DNAs that include (+Cy5) or exclude (−Cy5) covalently attached terminal Cy5.

FIG. 5A illustrates functionalization of antibody with succinimidyl-6-hydrazinonicotinate acetone hydrazine (SANH).

FIG. 5B illustrates functionalization of NH2-B' with succimidyl-4-formylbenzamide (SFB).

FIG. 5C illustrates the formation of UV traceable bisaryl hydrazone linkage between antibody and B'.

DETAILED DESCRIPTION

Figure 1A:
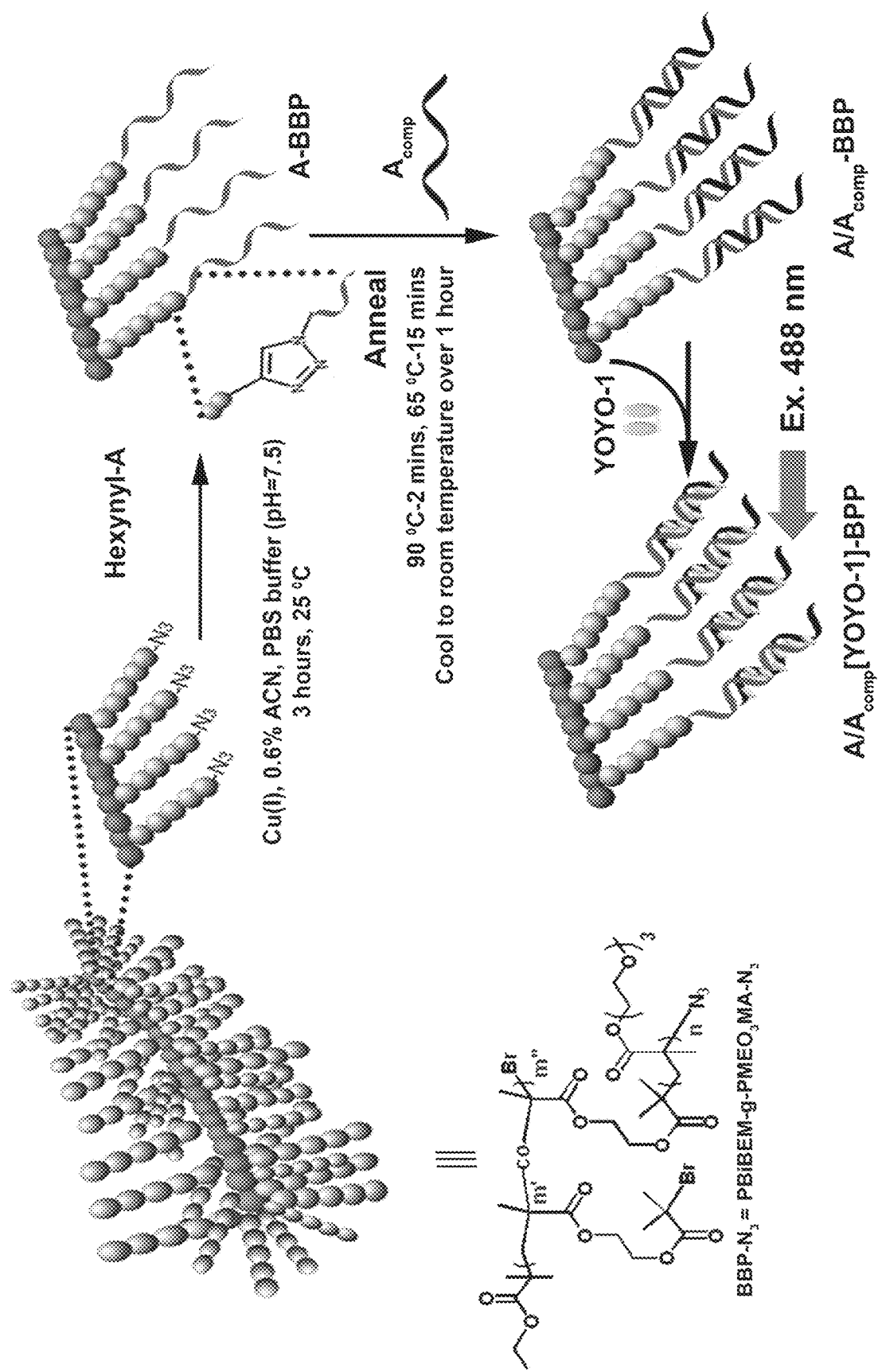
FIG. 1A illustrates schematically the assembly of a representative bottlebrush polymer (BBP) with azide side chain terminii by CuAAC or click reaction with hexynyl-DNA (red strand), resulting in single stranded DNA functionalized BBP (or DBBP), wherein annealing of complementary strands (Acomp) provide hundreds of base pairs for the intercalation of the fluorescent dye YOYO-1 (yellow) in double stranded DBBP, and wherein the inset shows the structure of the BBP-azide.

It will be readily understood that the components of the embodiments, as generally described and illustrated in the figures herein, may be arranged and designed in a wide variety of different configurations in addition to the described representative embodiments. Thus, the following more detailed description of the representative embodiments, as illustrated in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a fluorescent dye molecule" includes a plurality of such fluorescent dyes molecules and equivalents thereof known to those skilled in the art, and so forth, and reference to "the fluorescent dye molecule" is a reference to one or more such fluorescent dyes molecules and equivalents thereof known to those skilled in the art, and so forth. Recitation of ranges of values herein are merely intended to serve as a shorthand method of referring individually to each separate value falling within the range. Unless otherwise indicated herein, and each separate value, as well as intermediate ranges, are incorporated into the specification as if individually recited herein. All methods described herein can be performed in any suitable order unless otherwise indicated herein or otherwise clearly contraindicated by the text.

The term "polymer" refers generally to a molecule which may be of high relative molecular mass/weight, the structure of which includes repeat units derived, actually or conceptually, from molecules of low relative molecular mass (monomers). The term "copolymer" refers to a polymer including two or more dissimilar repeat units (including terpolymers—comprising three dissimilar repeat units—etc.). The term "oligomer" refers generally to a molecule of intermediate relative molecular mass, the structure of which includes a small plurality of units derived, actually or conceptually, from molecules of lower relative molecular mass (monomers). In general, a polymer is a compound having >1, and more typically >10 repeat units or monomer units, while an oligomer is a compound having >1 and <20, and more typically leas than ten repeat units or monomer units.

In a number of embodiments hereof, polymers having multiple extending chains, side chains or branches are used to attach double stranded or duplex nucleic acids thereto. In a number of embodiments, one strand of nucleic acid (a nucleotide or oligonucleotide) is covalently attached to the side chain, typically at a terminus thereof. More than one strand of nucleic acid may be attached to a chain. For example, a doubler or trebler linking moiety may be used to attach two or three, respectively, strands of nucleic acid to a chain. As second strand of nucleic acid, complementary to the first strand may then complexed to the first strand. In a number of embodiments hereof, the resultant duplexed nucleic acids are used to associate one or more fluorescent dye molecules (by intercalation and/or by covalent bonding) with the polymer-nucleic acid complexes hereof in forming fluorescent tags or labels. Increasing the number of fluorescent dye molecules associated with a label or tag hereof can increase the brightness of the label or tag. In the case that fluorescent molecules are to be intercalated, forming a duplex is required. However, in the case that fluorescent molecules/moieties are to be associated with the extending chains hereof only by covalent attachment, a single strand of nucleic acid or a duplex may be present on the extending chains.

The polymeric labels or tags hereof, when associated with an affinity binding or other targeting moiety (for example, via covalent bonding or via nucleic acid hybridization/complexing), are mobile within a liquid matrix (for example, in solution) or, for example, on membrane in a blot test. Example of affinity binding moieties for user herein include proteins (for example, antibodies), peptides (including cyclic peptides), aptamers (oligonucleotide or peptide molecules that bind to a specific target molecule), glycosides, and glycopeptides. As clear to those skilled in the art, the polymers of the compositions hereof, as well as the compositions, are soluble or dispersible in aqueous environments. When, for example, employed with a targeting moiety or probe which has a binding affinity for one or more target species, the conjugate composition is mobile in an aqueous sample to reach and interact with the target species. The polymers hereof may also be biocompatible. As used herein, the term "biocompatible" refers to polymers that are compatible with living cells, tissues, organs or systems, (that is, which do not produce substantial adverse effect—for example, by inducing excessive inflammation, excessive cytotoxicity or other excessive response in a living system), The polymers hereof can range broadly in the number and molecular weight of side chains or branches. Polymers hereof may, for example, include one hundred or more extending chains or branches. In general, the greater the number of side chains (that is, multiple extending chains), the greater the number of fluorescent dye molecules that may be associated with the label or tag, and the brighter the signal output. Polymers having multiple side chains or branches suitable for user herein include, but are not limited to, star-shaped polymers, comb polymers, dendrimers, graft polymers and brush or bottlebrush polymers. Star-shaped polymer or star polymers are branched or hyperbranched polymers in which a single branch point or a relatively short backbone chain gives rise to multiple linear side chains. Comb polymers include a main chain or backbone with two or more three-way branch points and linear side chains. A dendrimer is a repetitively branched polymer. Graft polymers/copolymers have one or more side chains that are different, structurally or configurationally, from the main chain or backbone of the polymer. Graft copolymers belong to the general class of segmented copolymers and generally include a linear backbone of one composition and randomly distributed branches of a different composition. The major difference between graft copolymers and bottlebrush polymers is the grafting density. Bottlebrush polymer have sufficient grafting density that the conformational and physical properties of brush polymers are affected by steric repulsion of the densely grafted side chains. High graft density along the backbone results is a significant degree of side chain/side chain interactions, particularly close to the polymer backbone, resulting in chain extension of the polymer backbone. Bottlebrush polymers may, for In general, polymer properties (including, polymer composition, size etc.) can be readily controlled in the labels or tags hereof for a particular application. Typically, in a bottlebrush polymer, the polymer backbone is longer than the chains extending therefrom. If the chains extending from a polymer backbone are longer than the backbone the polymer may be referenced as a star polymer.

The polymers hereof may, for example, be formed via a grafting from approach, in which the polymer backbone includes active sites capable of initiating functionality, or a grafting onto approach, in which the polymer backbone includes functional groups that are reactive with functional groups of a polymer or oligomer chain to be grafted onto the backbone. In either grafting from or grating onto approaches, Reversible-Deactivation Radical Polymerization (RDRP) procedures, as further described below, may be used to form the extending chains or branches.

Although, bright signal outputs are desirable for fluorescence detection of biomolecules at their native expression levels, simply increasing the number of labels on a probe, targeting species or targeting moiety often results in crowding-induced self-quenching of chromophores. Also, maintaining the function of the targeting species or moiety (for example, an antibody) is a concern when increasing the number of labels thereon. Representative embodiments hereof provide a simple method to accommodate hundreds or thousands of fluorescent dye molecules on a single probe, targeting species or targeting moiety (for example, an affinity binding probe such as an antibody) while avoiding the negative effects of self-quenching. In a number of embodiments, polymers including multiple side chains or branching such as bottlebrush polymer from which extend multiple (for example, hundreds) of duplex nucleic acid (for example, DNA) strands are used to accommodate, for example, hundreds of covalently attached and/or thousands of noncovalently intercalated fluorescent dye molecules. The polymer-nucleic acid assemblies or conjugates hereof are bright, prevent dissociation of the fluorophores, and can be tethered through, for example, nucleic acid hybridization to a probe (such as an IgG antibody) to make a bright fluorescent nanotag. Such an antibody (or other affinity binding entity) fluorescent nanotag may, for example, detect protein targets in flow cytometry, confocal fluorescence microscopy and dot blots with an exceptionally bright signal. The signal is at least an order of magnitude greater than current commercially available antibodies labeled with organic dyes or quantum dots.

The branched polymeric scaffolds hereof may thus incorporate many molecules of one or more fluorescent dyes. In a number of representative embodiments, the nano-labels or nanotags hereof are attached to a single antibody to provide a powerful fluorescent signal that is not achievable with current methods of labeling. In a number of embodiments, the polymeric scaffold extends hundreds of double stranded DNA from the side chains of a polymeric core to assemble intercalating fluorescent dyes. Brush-like polyremes provide flexible and compact architectures which, as discussed further below, provide stabilization of intercalated fluorescent dye molecules. In a number of representative embodiments, compositions, systems and methods hereof are discussed in connection with assemblies or conjugates of a bottlebrush polymer with nucleic acid (DNA) 'bristles' grafted to the side chains thereof. However, one skilled in the art will appreciate that any polymer including multiple side chains may be conjugated with nucleic acids for association with chromophore/dye molecules therewith. Nucleic acids are particularly effective scaffolds for fluorescent dyes and provide opportunities to design simple architectures for harnessing and efficiently transporting energy.

In a number of embodiments hereof, a Reversible-Deactivation Radical Polymerization procedure is use to form polymer side chains in conjugates hereof. Reversible-Deactivation Radical Polymerization (RDRP) procedures, formerly referred to as controlled radical polymerization (CRP) procedures, include, for example, Nitroxide Mediated Polymerization (NMP), Atom Transfer Radical Polymerization (ATRP), and Reversible Addition Fragmentation Transfer (RAFT) and others (including cobalt mediated transfer) that have evolved over the last two decades. RDRP provide access to polymer and copolymers comprising radically polymerizable/copolymerizable monomers with predefined molecular weights, compositions, architectures and narrow/controlled molecular weight distributions. Because RDRP processes can provide compositionally homogeneous well-defined polymers, with predicted molecular weight, narrow/designed molecular weight distribution, and high degrees of $\alpha$- and $\omega$-chain end-functionalization, they have been the subject of much study, as reported in several review articles and ACS symposia. See, for example, Qiu, J.; Charleux, B.; Matyjaszewski, K., $Prog.\ Polym.\ Sci.$ 2001, 26, 2083; Davis, K. A.; Matyjaszewski, K. $Adv.\ Polym.\ Sci.$ 2002, 159, 1; Matyjaszewski, K., Ed. Controlled Radical Polymerization; ACS: Washington, D.C., 1998; ACS Symposium Series 685. Matyjaszewski, K., Ed.; Controlled/Living Radical Polymerization. Progress in ATRP, NMP, and RAFT; ACS: Washington, D.C., 2000; ACS Symposium Series 768; and Matyjaszewski, K., Davis, T. P., Eds. Handbook of Radical Polymerization; Wiley: Hoboken, 2002, the disclosures of which are incorporated herein by reference.

A growing number of researchers have used RDRP procedures to prepare polymeric assemblies by grafting from surfaces or molecules functionalized with agents to control the selected RDRP procedure, particularly if it is of importance to control grafting density, molecular weight and composition of the tethered polymer/copolymer chain. Matyjaszewski and coworkers disclosed the fundamental four component ATRP process, comprising the addition, or in situ formation, of an initiator, in this case a molecule with a transferable atom or group that is completely incorporated into the final product, a transition metal and a ligand that forms, at least a partially soluble transition metal complex that participates in a reversible redox reaction with the added initiator or a dormant polymer to form the active species to copolymerize radically polymerizable monomers, in 1995.

The basic ATRP process and a number of improvements to the basic ATRP process have been described in a number of commonly assigned patents and patent applications including, for example, U.S. Pat. Nos. 5,763,546; 5,807,937; 5,789,487; 5,945,491; 6,111,022; 6,121,371; 6,124,411; 6,162,882; 6,624,262; 6,407,187; 6,512,060; 6,538,091; 6,541,580; 6,624,262; 6,627,314; 6,759,491; 6,790,919; 6,887,962; 7,019,082; 7,049,373; 7,064,166; 7,125,938; 7,157,530; 7,332,550; 7,407,995; 7,572,874; 7,678,869; 7,795,355; 7,825,199; 7,893,173; 7,893,174; 8,252,880; 8,273,823; 8,349,410; 8,367,051; 8,404,788; 8,445,610; 8,816,001; 8,865,795; 8,871,831; 8,962,764; 9,243,274; 9,410,020; Ser. Nos. 13/99,3521; 13/993,521; 14/239,181; 14/379,418; the disclosures of which are incorporated herein by reference.

ATRP has also been discussed in numerous publications with Matyjaszewski as co-author and reviewed in several book chapters. See, for example, Matyjaszewski, K. et al. $ACS\ Symp.\ Ser.$ 1998, 685, 258-283; $ACS\ Symp.\ Ser.$ 1998, 713, 96-112; $ACS\ Symp.\ Ser.$ 2000, 729, 270-283; $ACS\ Symp.\ Ser.$ 2000, 765, 52-71; $ACS\ Symp.\ Ser.$ 2000, 768, 2-26; $ACS\ Symposium\ Series$ 2003, 854, 2-9; $ACS\ Symp.\ Ser.$ 2009, 1023, 3-13; $ACS\ Symp.\ Ser.$ 2012, 1100, 1, and $Chem.\ Rev.$ 2001, 101, 2921-2990, the disclosures of which are incorporated herein by reference. These publications, for example, provide information on the range of suitable transition metals that can participate in the redox reaction and suitable ligands for the different transition metals to form transition metal complexes of differing activities suitable for polymerizing broad range of exemplified polymerizable (co)monomers in various solvents and under different activation procedures. See also *J. Am. Chem. Soc.*, 2014, 136, 6513-6533; and *Green Chemistry* 2014, 16, 1673, the disclosures of which are incorporated herein by reference.

ATRP is the most efficient RDRP method for the preparation of pure segmented copolymers, since, generally, unlike RAFT it does not require addition of a standard free radical initiator to continuously form new polymer chains that do not contain the desired α-functional group in a blocking from or a grafting from reaction thereby producing purer segmented or hybrid products. In addition, unlike NMP, ATRP does not require high temperatures to generate the active species by homolytic cleavage of the dormant chain end, which precludes direct formation of bioconjugates, in addition to possessing the capacity to copolymerize a much broader range of radically copolymerizable monomers than NMP.

ATRP allows the synthesis of α, ω-homo and heterotelechelic multi-segmented copolymers with a predetermined degree of polymerization, narrow molecular weight distribution (low $M_w/M_n$), incorporating a wide range of functional monomers and displaying controllable macromolecular structures under mild reaction conditions. ATRP generally requires addition or formation of an alkyl halide or (pseudo)halide as an initiator (R—X) or dormant polymer chain end ($P_n$—X), and a partially soluble transition metal complex (Cu, Fe or Ru, for example) capable of undergoing a one electron redox reaction as a catalyst (although metal free ATRP procedures have recently been developed). See, for example, *ACS Macro Letters* 2015, 4, 192-196, the disclosure of which is incorporated herein by reference. The generally accepted mechanism of an ATRP reaction is shown below

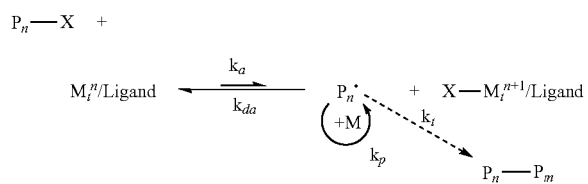

The methods of atom transfer radical polymerization (ATRP) have thus yielded rich and diverse polymer architectures. In a number of embodiments, extending chains, side chains or branches of polymers hereof may, for example, be grown/grafted from initiators or from sites of a transfer agent under aqueous conditions or in the presence of a polar solvent. The extending polymer chains may, for example, be hydrophilic or water soluble. In representative embodiments, the monomers for copolymerization in a grafting from approach may, for example, include an oligo (ethylene oxide) methacrylate (OEOMA). In general OEOMA monomers are available in higher purity than other commercially available biocompatible oligo(ethylene oxide) methacrylates. Many other monomer are also suitable for user herein such as Di(ethylene glycol) methyl ether methacrylate ($MEO_2MA$), 2-(Dimethylamino)ethyl methacrylate, DMAEMA, acrylamide (AAm), N,N-dimethylacrylamide (DMA), and N-vinylimidazole (VI), N-isopropylacrylamide (NIPAM) and 2-(methylsulfinyl) ethyl acrylate (MSEA). Representative polymers side chains include, for example, chains of poly(monomethoxy poly (ethylene glycol)-(meth)acrylate) (PPEG(M)A), poly(N-isopropylacrylamide) (PNIPAM), and poly(N,N-dimethylacrylamide) (PDMA).

In a number of embodiments, the degree of polymerization of side chain in a star, brush and other graft macromolecule is sufficiently high to facilitate relatively high yield of, for example, a click reaction to tether a strand of nucleic acid to the side chains and so a complementary strand nucleic acid may be complexed therewith. In a number of representative embodiments, a degree of polymerization of at least 25, at least 40 or at least 50 is achieved. In a number of embodiment, the backbone length is equal to or longer than the longest side chain length.

Figure 1B:
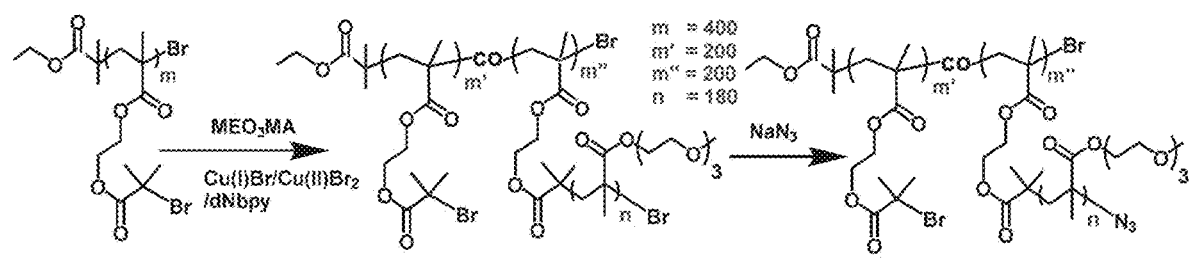
FIG. 1B illustrates synthesis of a representative bottle-brush polymer of BBP used in the studies hereof.

For a scaffold that could display a large and functionalizable array, a representative bottlebrush polymer (BBP) with reactive azide groups at the tips of the bristles was synthesized as illustrated in FIGS. 1A and 1B. As illustrated in FIG. 1B, to obtain the BBP core, a poly[2-(2-bromoisobutyryloxy)ethyl methacrylate] (PBiBEM) macro-initiator with a degree of polymerization of 400 (m), was used as the backbone. From the PBiBEM core, approximately half of the bromoisobutyrate groups initiated the side chains, leading to grafting of 200 (m") side chains with 2-(2-(2-methoxyethoxy)ethoxy)ethyl methacrylate ($MEO_3MA$) monomeric units. The 50% initiation efficiency was calculated based on the content of the azide groups, and it can be related to the large size of the monomer with long PEO substituent. The degree of polymerization of side chains was calculated based on absolute molecular weight of the bottlebrush measured by light scattering ($Mn=8.6\times10^6$) yielding n=180. The bromides at the side chain termini were then substituted with azides to provide the BBP-$N_3$. The "clickable" bottlebrush polymers hereof provide a high density of side chains for subsequent functionalization with a 5'-hexynyl modified DNA sequence (hexynyl-A in FIG. 1A; Sequence ID no. 1 in the Sequence Listing hereof). These DNA sequences could, for example, be grafted to the side chain termini via a Cu(I)-catalyzed azide alkyne cycloaddition ('click') reaction. The pseudo-ligandless click conditions may be optimized for nucleic acid conjugations in a buffered solution (phosphate buffered saline (PBS), pH 7.5) with acetonitrile as a minor co-solvent. Three hours of reaction time was sufficient for near quantitative reaction of the DNA to the BBP with the disappearance of the azide peak at 2110 $cm^{-1}$ in aqueous phase FTIR confirming the completion of the reaction. Simple purification using molecular weight cut-off filters provided the single stranded conjugate, A-BBP with about 200 DNA strands per brush.

Many types of click reactions may be used in the compositions hereof. Examples of suitable click reactions for use herein include, but are not limited to, Staudinger ligation, azide-alkyne cycloaddition (either strain promoted or copper (I) catalyzed), reaction of tetrazine with trans-cyclooctenes, disulfide linking reactions, thiolene reactions, hydrazinealdehyde reactions, hydrazine-ketone reactions, hydroxyl aminealdehyde reactions, hydroxyl amine-ketone reactions and Diels-Alder reactions. In such click reactions to attach a first moiety to a second moiety, one of the functional groups of the click reaction is on the first moiety and the other of the functional groups of the click reaction is on the second moiety.

To determine the number of bristles on the bottlebrush polymer, it was first assumed that there were 400 azide-terminated side chains (corresponding to a grafting efficiency or 100%). When hexynyl-DNA and azide from BBP are reacted in an equimolar ratio based on this assumption, half of the hexynyl DNA was recovered from the filtrate during the product isolation from molecular weight cut off filters (30 kDa). However, when the product (DBBP) was tested using FTIR spectrometry, the azide peak had completely disappeared indicating that all the azides in BBP reacted with DNA. Therefore, it was concluded that there was an average of 200 rather than 400 azide-terminated side chains (that is, bristles) per brush.

Figure 1C:
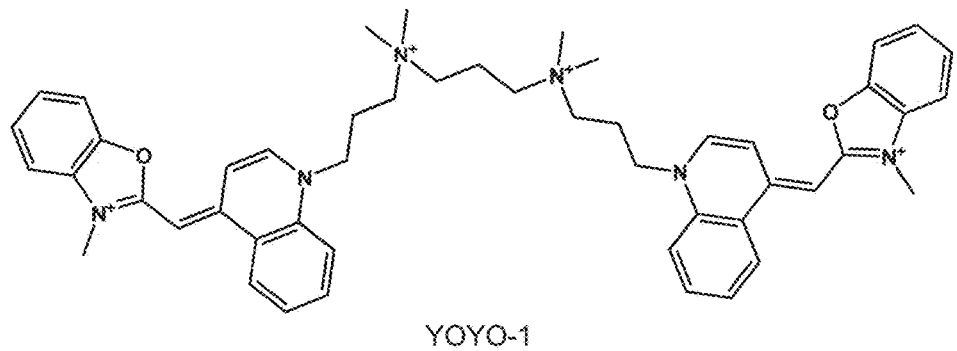
FIG. 1C illustrates the chemical structure of YOYO-1.
Figure 1D:
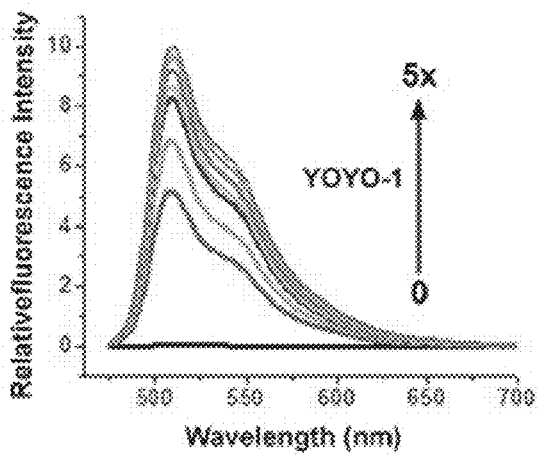
FIG. 1D illustrates a graph of increasing fluorescence intensities ($\lambda$ex=488 nm) with increasing YOYO-1 up to 5 equivalents relative to DNA.
Figure 1E:
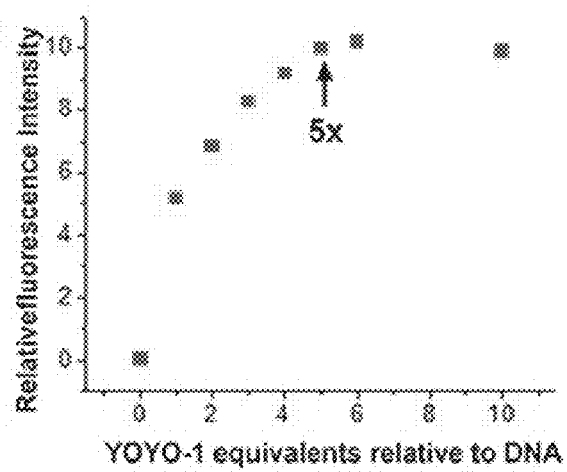
FIG. 1E illustrates a graph of the fluorescence emission at 510 nm versus YOYO-1 equivalents relative to DNA concentration and shows the saturation of the DBBP with YOYO-1 occurs around 5 equivalents as expected.

Complexing or annealing of a complementary strand or DNA (Acomp in FIGS. 1A and 1F; Sequence ID No. 3 in the incorporated Sequence Listing) completes the formation of the full DNA-BBP (DBBP) scaffold, A/Acomp-BBP. With about 200 double stranded DNAs (dsDNA) per brush, this DBBP can accommodate >1000 intercalating fluorescent dyes. For the DNA intercalating fluorescent dye, YOYO-1 was chosen as a representative example, YOYO-1 is a commercially available dimer of oxazole-yellow (see FIG. 1C) which has a higher affinity for dsDNA than the monomeric counterpart. By titrating YOYO-1 into the A/Acomp-BBP scaffold, the fluorescence intensity at 510 nm could be monitored to determine the loading of the scaffold with dye. As illustrated in FIG. 1D, the fluorescence increases monotonically with the accommodation of one YOYO-1 bisintercalator per four DNA base pairs (bp), and begins to approach saturation with approximately five YOYO-1 dimers per dsDNA (see the arrow in FIG. 1E). When bound to dsDNA, YOYO-1 has an extinction coefficient of 98 900 $M^{-1}$ $cm^{-1}$ at 491 nm. Given that there are, on average, 200 dsDNAs per brush with 18 bp/duplex and 2 overhanging bases, at the saturation point with five YOYO-1 dimers, the extinction coefficient of the YOYO-1 loaded DBBP scaffold (A/Acomp [YOYO-1]-BBP) reaches ~$10^8$ $M^{-1}$ $cm^{-1}$.

It is often desirable to red shift the emission wavelength away from the excitation wavelength to minimize the background autofluorescence, particularly in biological samples. Wavelength shifting can be achieved by allowing the light-absorbing chromophores (donors) to transfer the excitation energy to lower energy acceptor chromophores that can fluoresce at a longer wavelength. To incorporate a wavelength shifting property to the DBBP scaffold, the complementary strand was designed with a terminal acceptor cyanine-5 (Cy5) dye (Cy5-Acomp in FIG. 1F).

Efficient energy transfer (ET) between YOYO-1 and Cy5 (see FIG. 2A) has been demonstrated. Such ET is clearly observed in the fluorescence emission spectrum of the DNA-BBP with the peak maximum emerging at 665 nm while a drop occurs in the YOYO-1 fluorescence at 510 nm (see arrows in FIG. 2B). Based on the quenching of YOYO-1 emission in the presence of Cy5, the ET efficiency is estimated to be 52%. The emission spectrum of a control sample with the same concentration of the A/Cy5-Acomp dsDNA free in the buffered solution (i.e., non-brush DNA) shows ET but at a lower efficiency compared to DBBP (see FIG. 2C). The brush immobilized DNA shows higher ET compared to non-brush DNA in solution. The traces in FIGS. 2B and 2C correspond to DNAs that include (+Cy5 in FIG. 2B) or exclude (−Cy5 in FIG. 2B), respectively, covalent terminal Cy5 on all the hybridized DNA strands. The ET is calculated based on the drop in fluorescence at 510 nm (cyan arrow). Although the double-strand DNA (dsDNA) sequences are identical, (and without limitation to any mechanism) their three-dimensional arrangement and localization around the polymeric core likely leads to the enhanced ET efficiency through an interduplex mechanism, which would not be possible for the dsDNA in dilute solution.

As described above, the DBBP contains about 200 Cy5 dyes incorporated through hybridization of a Cy5-labeled strand to the clicked complement present at the tips of the brush bristles. Direct excitation of Cy5 in the DBBP versus free DNA duplex revealed no significant difference in Cy5 fluorescence intensity, indicating a lack of self-quenching even within the relatively dense environment of the DBBP (see FIGS. 2E and 2F). Without limitation to any mechanism, this observation could result from stacking of Cy5 dyes on the ends of their respective duplexes. In contrast, when the samples are excited in the YOYO-1 absorption band, significantly stronger Cy5 emission is observed for the DBBP, as a result of the more efficient energy transfer in the polymeric material.

Figure 2D:
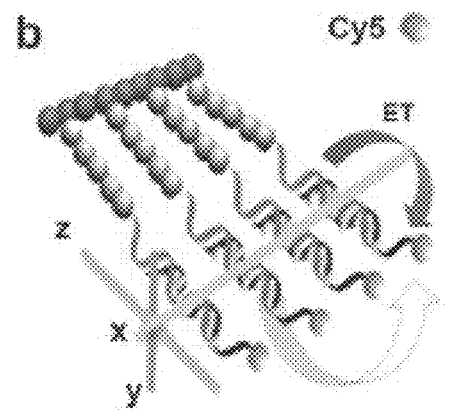
FIG. 2D illustrates schematically the manner in which brush DNA assembles dye molecules at a high local density in a network of adjacently located YOYO-1 dyes, wherein the YOYO-1 dyes located in x, y and z directions of the brush-DNA scaffold can contribute cooperatively to ET by both intra- and inter-duplex mechanisms.
Figure 2E:
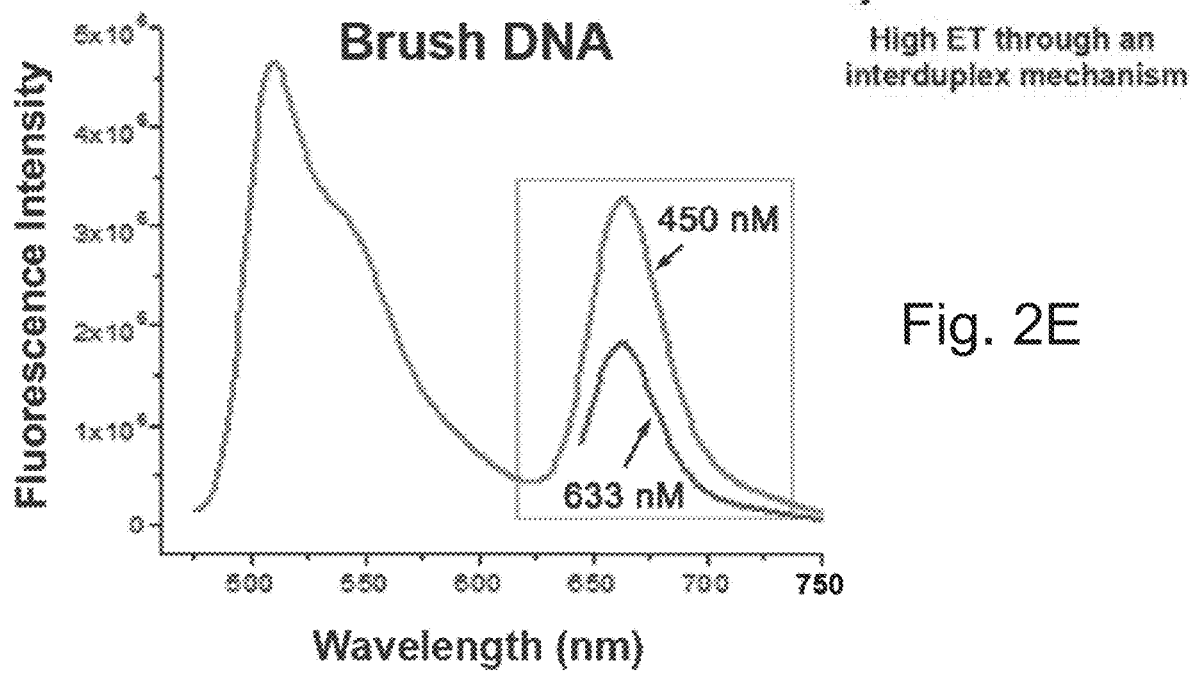
FIG. 2E illustrates a fluorescence intensity spectra for Brush DNA wherein the box highlights the higher ET in the brush DNA as the fluorescence emission is greater when excitation is at 450 nm through the YOYO-1 than when Cy5 is directly excited at 633 nm.
Figure 2F:
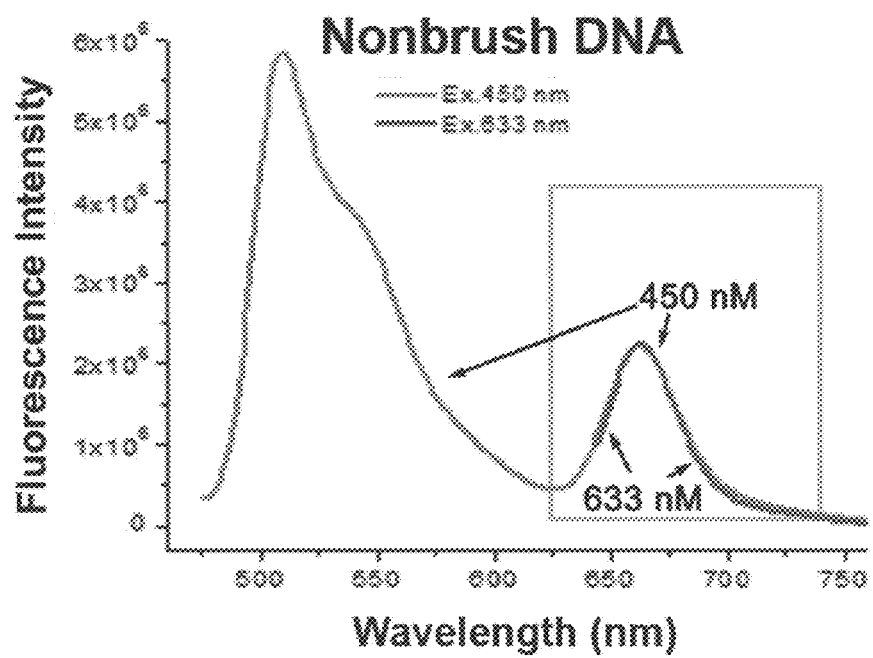
FIG. 2F illustrates a fluorescence intensity spectra for Non-brush DNA wherein the box highlights that no difference is observed when excitation is at 450 nm or excitation is at 633 nm.

As illustrated in FIG. 2D, the brush-DNA assembles the dyes at a high local density in a network of adjacently located YOYO-1 dyes. The YOYO-1 dyes located in x, y and z directions of the brush-DNA scaffold can contribute cooperatively to ET by both intra- and inter-duplex mechanisms. In FIGS. 2D and 2E, the boxes highlight the higher ET in the brush DNA. The fluorescence emission is greater when excitation is at 450 nm through the YOYO-1 than when Cy5 is directly excited at 633 nm in brush-DNA (FIG. 2E), whereas no such difference is observed in non-brush DNA (FIG. 2F).

Figure 3A:
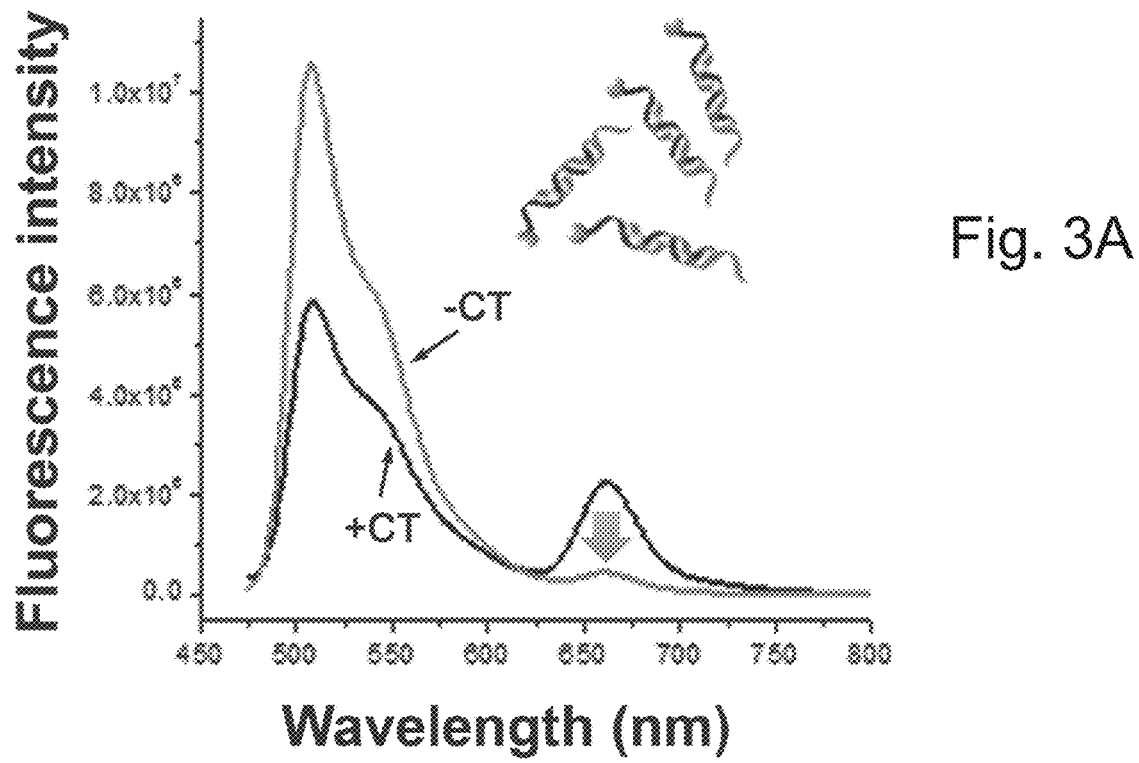
FIG. 3A illustrates a fluorescence intensity spectra for Non-brush DNA (that is, free DNA in solution) before (-CT) and after (+CT) addition of calf thymus (CT) DNA in four times excess of A/Cy5-Acomp[YOYO-1].

While the ease of assembly of intercalating dyes in a DNA based scaffold is appealing, the dissociation of dyes from the intercalating sites can lead to reduced brightness and non-specific staining. It has been reported that bisintercalating YOYO-1 readily dissociates from a DNA three-way junction in the presence of excess calf thymus (CT) DNA. Therefore the stability of the DBBP nanotag was tested by adding a four-fold excess of CT (in base pairs). In these experiments, DBBP-bound YOYO-1 can undergo ET to nearby Cy5 dyes, so dissociation of the intercalator with subsequent binding to CT DNA should result in a decrease in ET. This result was observed for a control experiment in which YOYO-1 was pre-bound to a free (i.e. non-brush) Cy5-labeled DNA duplex and then mixed with excess CT DNA. As illustrated in FIG. 3A, an immediate drop in ET upon addition of CT DNA was observed, consistent with rapid dissociation of the intercalator from the free DNA duplex.

Figure 3B:
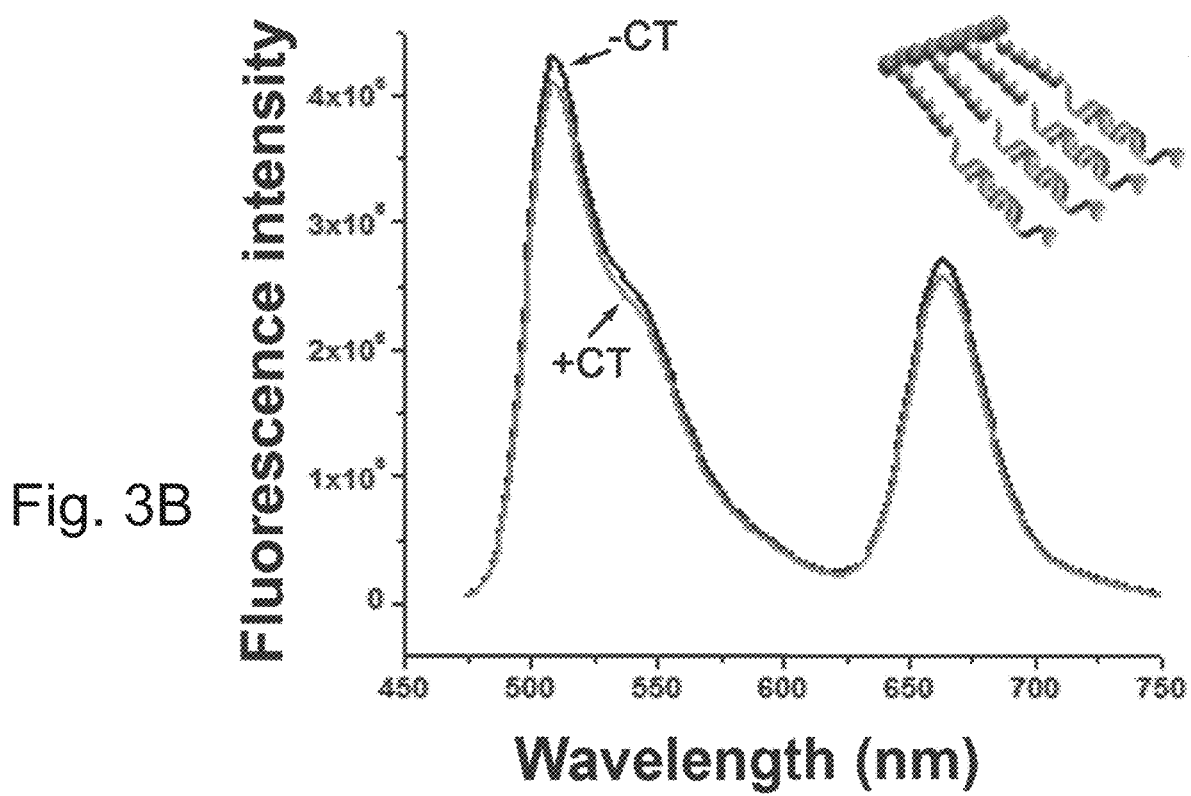
FIG. 3B illustrates a fluorescence intensity spectra for Brush DNA before (−CT) and after (+CT) addition of calf thymus (CT) DNA in four times excess of A/Cy5-Acomp [YOYO-1].
Figure 3C:
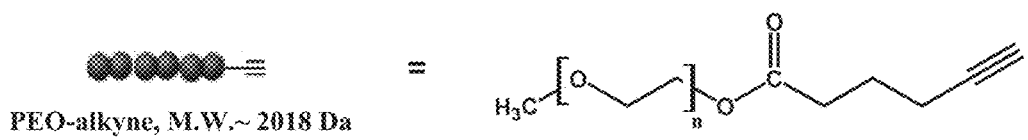
FIG. 3C illustrates the structure of PEO-alkyne and synthesis of DNA bottlebrush polymers with lower loading of DNA.
Figure 3C:
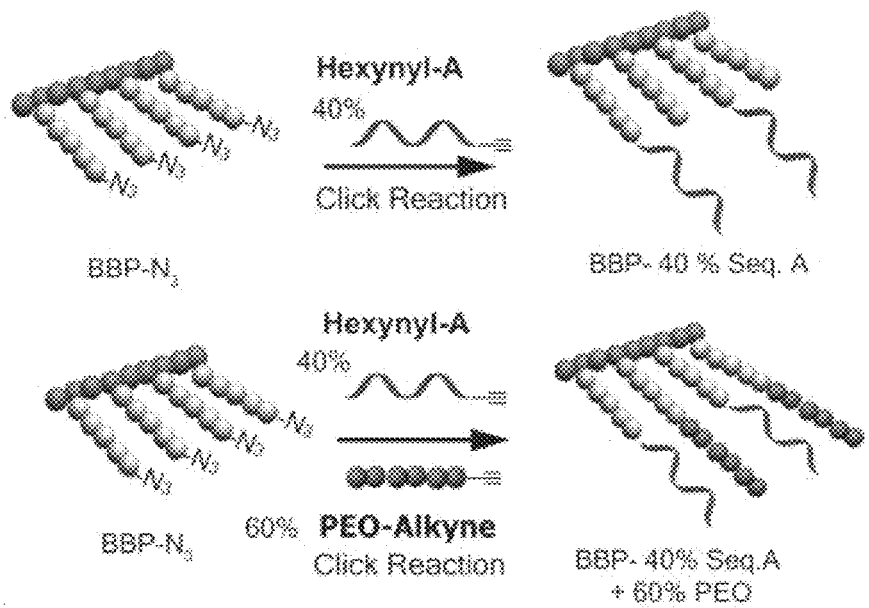
Figure 3D:
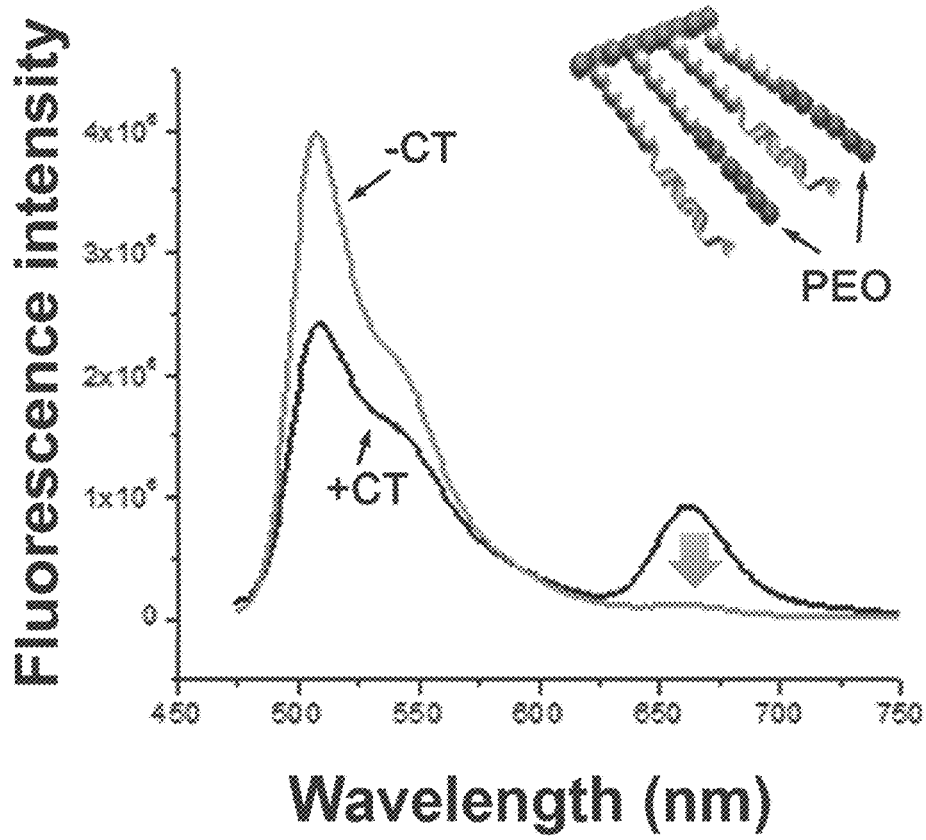
FIG. 3D illustrates a fluorescence intensity spectra for Brush DNA before (−CT) and after (+CT) addition of calf thymus (CT) DNA in four times excess of A/Cy5-Acomp [YOYO-1] for a brush with lower (that is, 40% lower) DNA loading and including polyethylene oxide (PEO) chains.

In stark contrast, when CT DNA is added to the YOYO-1 loaded DBBP, the ET signal remained unchanged, even after 15 hours, indicating that the polymeric scaffold with dsDNA facilitates retention of the intercalators (see FIG. 3B). Without limitation to any mechanism, the strong retention of YOYO-1 by the DBBP may be attributed to the electrostatic attraction between the tetracationic intercalating dye and the relatively dense polyanionic DNA assembly, as opposed to free DNA, where the negative charge density of the Cy5-labeled duplex is equivalent to that of the unlabeled CT-DNA competitor. To support this, a scaffold was designed with a reduced loading of DNA (that is, 40% less) as illustrated in FIG. 3C. To compensate for the total packing of strands extending from the polymeric core, poly(ethylene oxide) (PEO) was also incorporated to react with the remaining azide groups (60%) of the BBP during the click conjugation reaction (see FIG. 3C). The completion of the reaction of the azide groups was verified by aqueous phase FTIR. After pre-loading with YOYO-1 and mixing with CT-DNA, an immediate drop in ET was observed as illustrated in FIG. 3D. This result is consistent with the attribution that the greater negative charge density on the fully dsDNA loaded brush plays a significant role in suppressing the dissociation of YOYO-1.

Figure 4A:
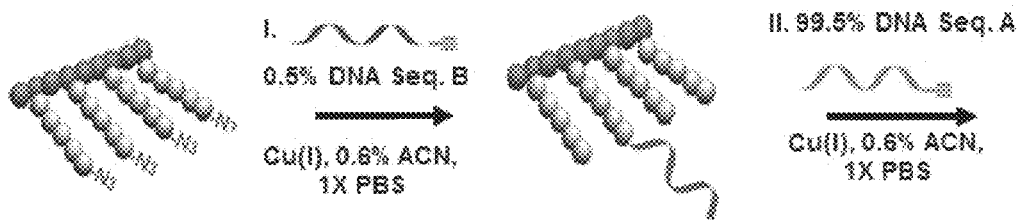
FIG. 4A illustrates the preparation of a DNA bottlebrush polymer hereof with a strand of DNA (sequence B) different from strand A for complexing an affinity binder (for example, an antibody) or other targeting moiety having a strand of DNA complementary to the different strand of DNA.
Figure 4B:
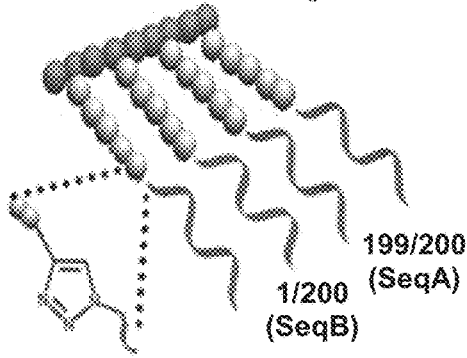
FIG. 4B illustrates schematically the preparation of a nano-label or nanotag hereof based upon tethering an antibody to the DBBP of FIG. 4A, wherein the DBBP can be hybridized to Cy5-Acomp (via attached sequence A) and to an antibody bearing a fully complementary B'comp strand (via attached sequence B) and, subsequently, loaded with YOYO-1, and wherein the single sequence B per bottlebrush polymer was used to ensure attachment of one antibody per brush.
Figure 4B:
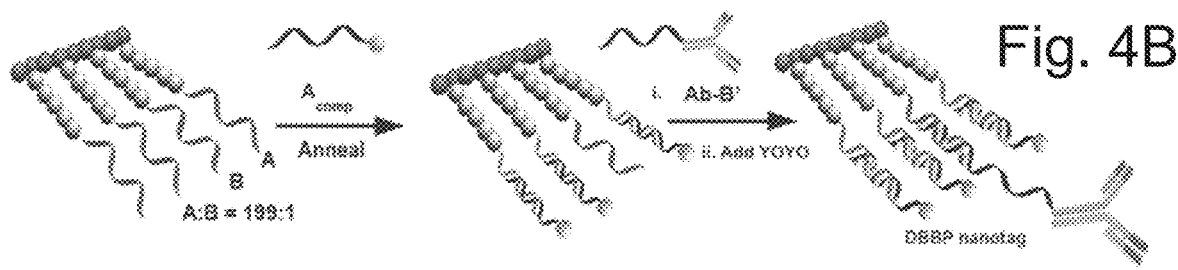
Figure 4C:
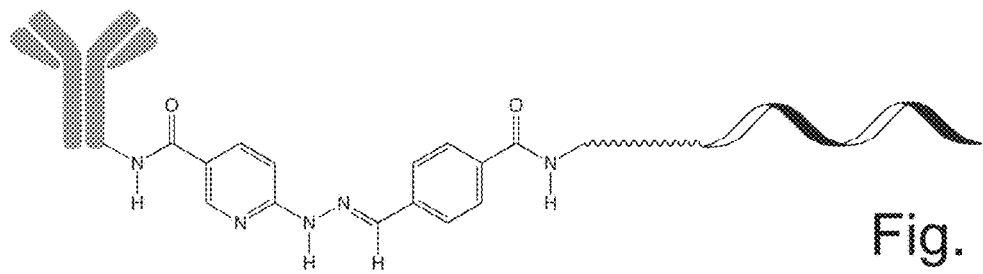
FIG. 4C illustrates schematically a representative embodiment of a c-myc protein detection system using primary and secondary antibody interactions, wherein the nanotag or label (X) is tethered to the secondary antibody.

In a number of further studies, dye-loaded DBBPs hereof were used as fluorescent nanotags or nano-labels for labeling applications. In representative studies, a DBBP was conjugated to a secondary IgG antibody for specific targeting as illustrated in FIGS. 4A through 4D. Functionalization of secondary antibodies is appealing because a single secondary antibody can be used with many different primary antibodies generated against diverse antigens. It has been shown DNA hybridization can be used to generate protein-polymer hybrids. Furthermore it was demonstrated that an antibody-DNA nanotag conjugate may be constructed through hybridization of dye-labeled DNA strands to a secondary antibody labeled with the complementary DNA strand. This approach was used so that a DNA strand on the DBBP could be used to hybridize to a complementary strand covalently conjugated to an antibody. The antibody was functionalized with an average of one DNA strand through a bisaryl hydrazone linkage as illustrated in FIG. 4C. The IgG conjugated 23-mer strand A' (Sequence ID No. 4 in the incorporated Sequence Listing) is fully complementary in sequence to strand A on the DBBP, unlike the Cy5-Acomp strands that include 5 unpaired overhanging residues. Thus, the greater stability of the 23-mer was relied on to be able to hybridize the DBBP to the IgG. To favor hybridization of a single antibody to each brush, a DBBP was synthesized in which two different DNA sequences were clicked onto the bristles as illustrated in FIGS. 4A and 4B. Using proportionally 0.5% of one DNA sequence (sequence B; Sequence ID No. 2 in the incorporated Sequence Listing)) along with the previous sequence A during the click reaction gave, on average, a single copy of sequence B on each brush (as each brush has 200 azides available for functionalization). This separate sequence B is fully complementary to the antibody (Ab) conjugated DNA sequence (sequence B, Sequence ID No. 5 in the incorporated Sequence Listing). The remaining (199) DNA sequences on the brush were hybridized as previously described to the Cy5 bearing complementary strand, Cy5-Acomp, to give the final DBBP-nanotag as illustrated in FIG. 4B. As clear to one skilled in the art, sequence A or another sequence may be used to complex to an affinity binding moiety including a complementary strand of nucleic acid. Moreover, an affinity binding moiety by be covalently attached to the polymer hereof via coupling/reactive functionalities (using, for example, a click reaction as described herein).

Figure 4D:
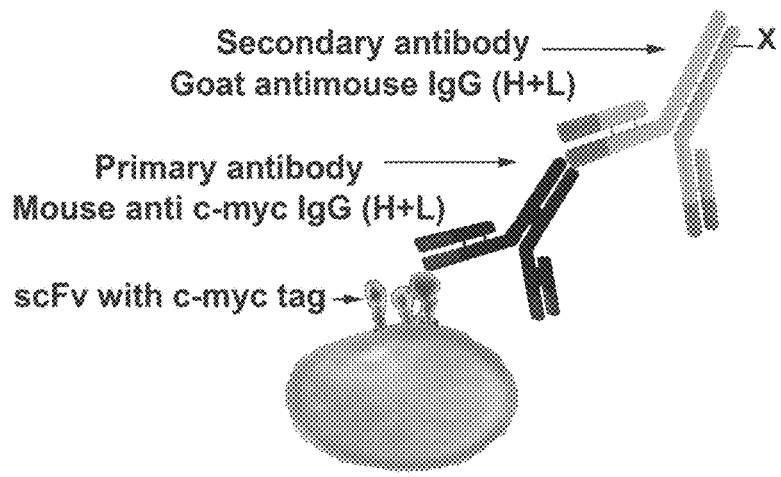
FIG. 4D illustrates a UV traceable bisaryl haydrazone linkage between an antibody and a DNA nucleotide used for conjugation of the antibody to the DNA bottlebrush polymers hereof.
Figure 4E:
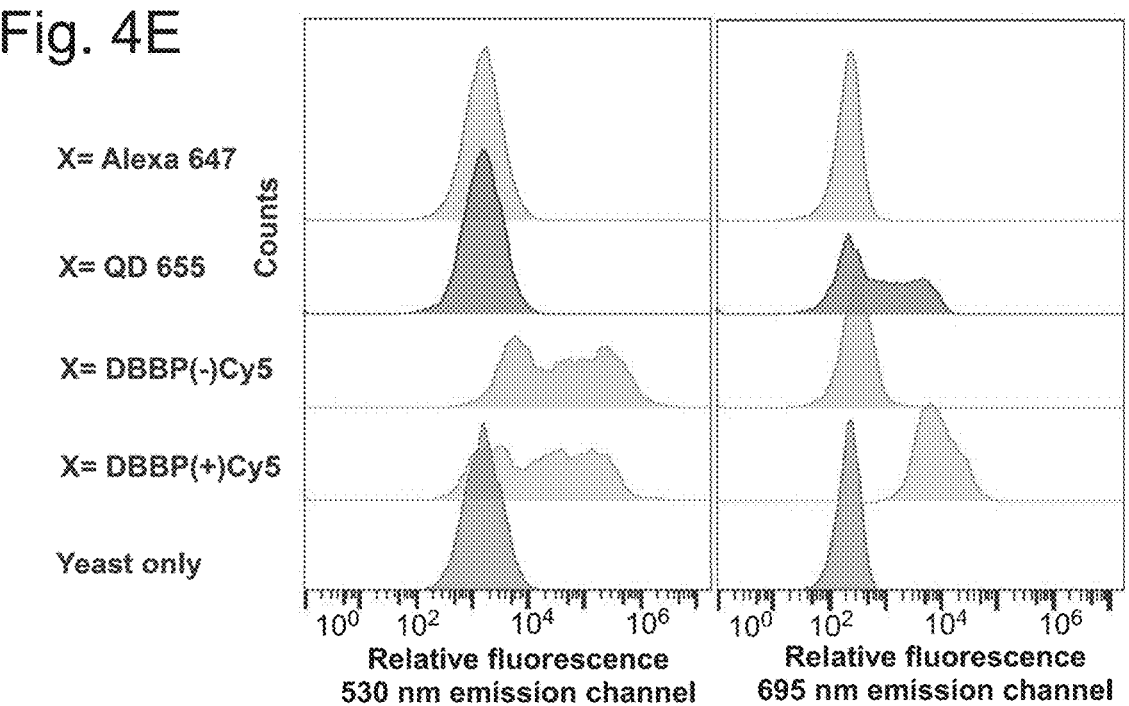
FIG. 4E illustrates flow cytometry data showing high fluorescent brightness of a representative brush nanotag hereof compared to commercially available antibody tags.

DBBP nanotag of FIG. 4B was tested on yeast cells that expressed on their surface a single chain variable fragment (scFv) with a c-Myc binding epitope as illustrated in FIG. 4D. After incubation with a primary antibody specific for the c-Myc epitope, the cells were stained with the secondary IgG antibody bearing the fluorescent DBBP for analysis by flow cytometry and microscopy. The representative DBBP nanotag was tested on yeast cells that expressed on their surface a single chain variable fragment (scFv) with a c-Myc binding epitope. After incubation with a primary antibody specific for the c-Myc epitope, the cells were stained with the secondary IgG antibody bearing the fluorescent DBBP for analysis by flow cytometry and microscopy. Commercially available Alexa 647 and Quantum Dot (QD) 655 tagged goat anti-mouse secondary IgGs were used as controls and comparison. Based on the histograms and the mean fluorescence values as illustrated in FIG. 4E, the DBBP based nanotags are at least an order of magnitude brighter compared to the QD-655 tagged antibody labels. At the same secondary antibody concentration as that of the DBBP nanotag (50 nM), the commercially available Alexa 647-conjugated probe gives only baseline fluorescence intensity. The signal from emission channel at 695 nm significantly increases when the DBBP scaffold contains Cy5 dyes. In addition to demonstrating the significantly higher brightness of DBBP-conjugated antibodies, these results suggest that although a rather large polymer brush DNA conjugate (120× 20 nm) is tethered to the antibody, antigen binding is not hindered.

Figure 4F:
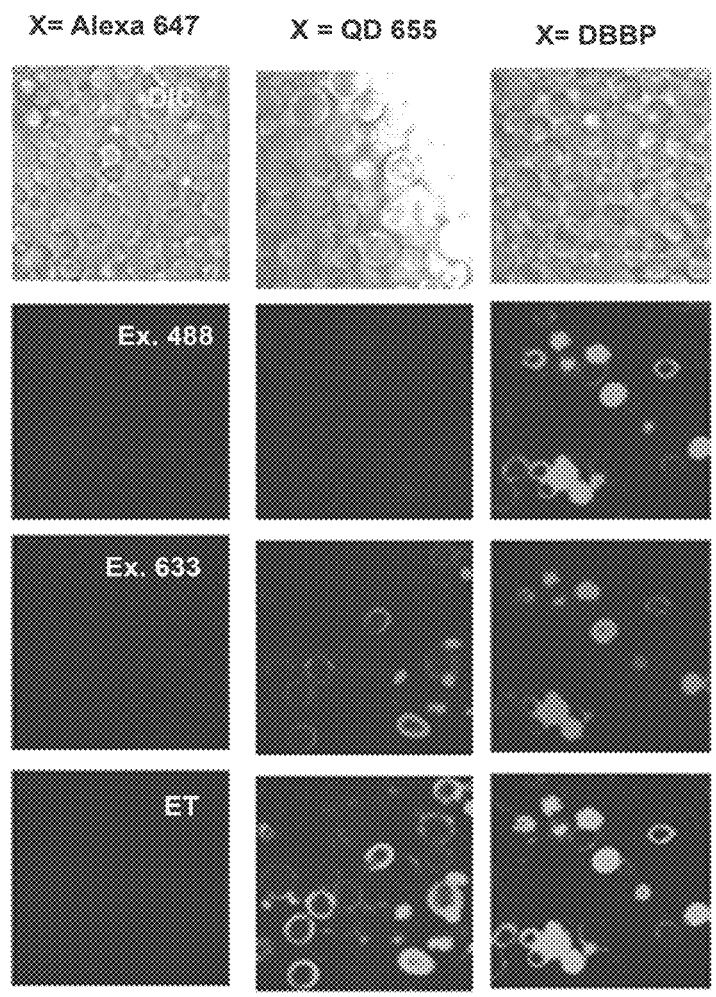
FIG. 4F illustrates confocal microscopic images showing the increased brightness of representative nanotag antibodies hereof compared to commercially available ALEXA FLUOR 647®-tagged (a fluorescent tag available from Thermo Fisher Scientific of Waltham, Mass.) and QD655-tagged (a fluorescent tag available from Thermo Fisher Scientific) antibodies

The confocal images shown in FIG. 4F reinforce the flow cytometry results. Under the conditions of the studies, the Alexa 647-labeled antibody failed to stain the cells, while staining is evident for the QD 655 and DBBP-tagged antibodies. Similar labeling experiments were also performed using biotin coated polystyrene beads by changing to a mouse anti-biotin primary antibody. In both flow cytometric and confocal imaging experiments, the DBBP nanotags again were an order of magnitude brighter than the commercially available probes. The efficient but incomplete ET in the DBBP allows strong staining to be observed in all three channels. Given the brightness of the DBBP nanotag, the reliance on ET to shift the emission away from autofluorescence is likely unnecessary, since any background signal will be much weaker than the specific staining resulting from the DBBP. Furthermore, while control over the extent of functionalization of the antibody was optimized, the conjugation was not directed to a specific residue on the protein. With emerging methods for greater control and specific attachment of DNA and/or other nucleic acids to antibodies, the hybridization method can be even more powerful for the development of probes.

Figure 4G:
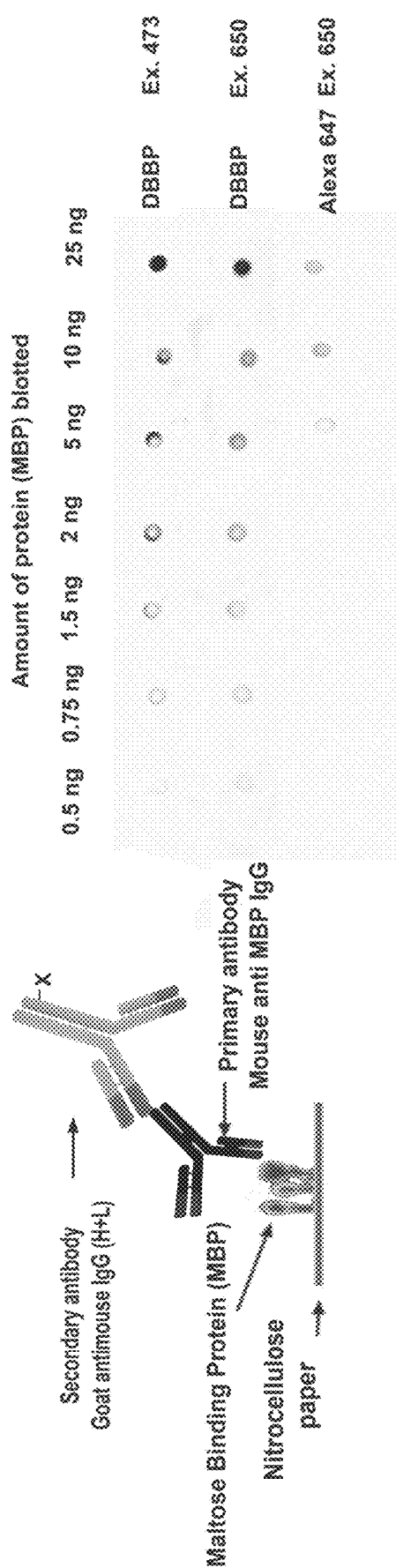
FIG. 4G illustrates the detection of maltose binding protein (MBP) using representative primary and secondary antibody system hereof and the visual confirmation of the specificity and brightness of DBBP nanotags via dot blots, wherein the nanotag antibodies hereof allow visualization with at least an order of magnitude greater sensitivity compared to commercially available systems.

The studies hereof were also extended to dot blots, a widely used format for screening and detection of specific bio-molecules. This represents a simplification of the northern blot, Southern blot, or western blot methods. To evaluate the efficiency of the DBBP nanotag in this method, maltose binding protein (MBP) was chosen as a target. MBP is part of the maltose/maltodextrin system of $Escherichia\ coli$, which is responsible for the uptake and efficient catabolism of maltodextrins. An anti-MBP monoclonal primary antibody sandwiched between the MBP target blotted on a nitrocellulose paper, with the DBBP nanotag was chosen as the detection system (see FIG. 4G). Increasing amounts of MBP blotted on the paper could be detected with the DBBP nanotag, as shown by increasing density of the spots in FIG. 4E. The paper was excited at either 473 nm (YOYO-1) or 650 nm (Cy5 or Alexa 647) and the emission was recorded at 695 nm. At both excitation wavelengths, as little as 0.5 ng MBP could be detected by eye for the DBBP-conjugated antibody. The observation of discrete spots for excitation of YOYO-1 indicates that the dye remains sequestered by the DNA within the polymer brush, instead of nonspecifically staining the paper. In separate experiments using an antibody conjugated to a DNA tetrahedron nanotag, YOYO-1 was not retained by the antibody, leading to strong nonspecific background fluorescence from the paper. The control experiment performed under similar conditions with an Alexa 647-tagged secondary antibody gave a detection limit of 5 ng of MBP protein. The DBBP nanotag is thus a versatile and bright multichromophore system for labelling applications.

The use of a nucleic acid-(DNA)-conjugated bottle-brush polymer as a brightly fluorescent nanotag that is useful in applications for sensitive detection of proteins both in blots and directly on cell surfaces has been demonstrated herein. In particular, it has been shown that the polymer brush architecture provides the means to graft nucleic acid side chains at a high local density. The conjugation of nucleic acid to the polymeric scaffold is readily achieved via, for example, the high efficiency Cu(I) promoted azide-alkyne cycloaddition reaction with a simple filtration to purify the brush-nucleic acid conjugate. These brush localized nucleic acid (for example, DNA) bristles provide a dense scaffold for intercalating fluorescent dyes such as YOYO-1, generating extinction coefficients as much as ~$10^8$ $M^{-1}$ $cm^{-1}$ per nanotag. Importantly, the intercalated YOYO-1 dyes are retained on the DBBP scaffold without dissociation, avoiding complications from background fluorescence. This property eliminates the need for obligatory covalent conjugation of dyes and tremendously eases the assembly of thousands of fluorescent dyes via simple mixing. The representative approach of using DNA bristles on the polymer brush provides access to scaffolds with the same donor chromophore but with additional and different terminal acceptor dyes at the end of the DNA strands. The ability to excite each fluorescent scaffold at a single wavelength while monitoring emission in different channels enables multiplex detection schemes involving antibodies labeled with unique DBBPs. The high degree of control over the sequences on the brush allows us to tailor specific sequences for attaching targeting agents through simple hybridization and without any further modification to the generic scaffold design. In the representative examples described herein, conjugation of the large DBBP to a secondary antibody through DNA hybridization does not hinder the antibody's binding. It was shown that these versatile DBBP nanotags on antibodies provide probes that are at least ten times brighter than commercially available QD or Alexa fluor-tagged IgG antibodies. By lengthening the nucleic acid sequences (to provide more intercalation sites) or the number of nucleic acid strands on the brushes, it is possible to increase the chromophore content of the antibody nanotags even further. Using other targeting agents such as an internalizing antibody or an aptamer or using smaller brushes that are approximately spherical in shape which can enter cells expands the technology to detect targets in internal cell compartments or for other types of in vitro detection assays.

Figure 7:
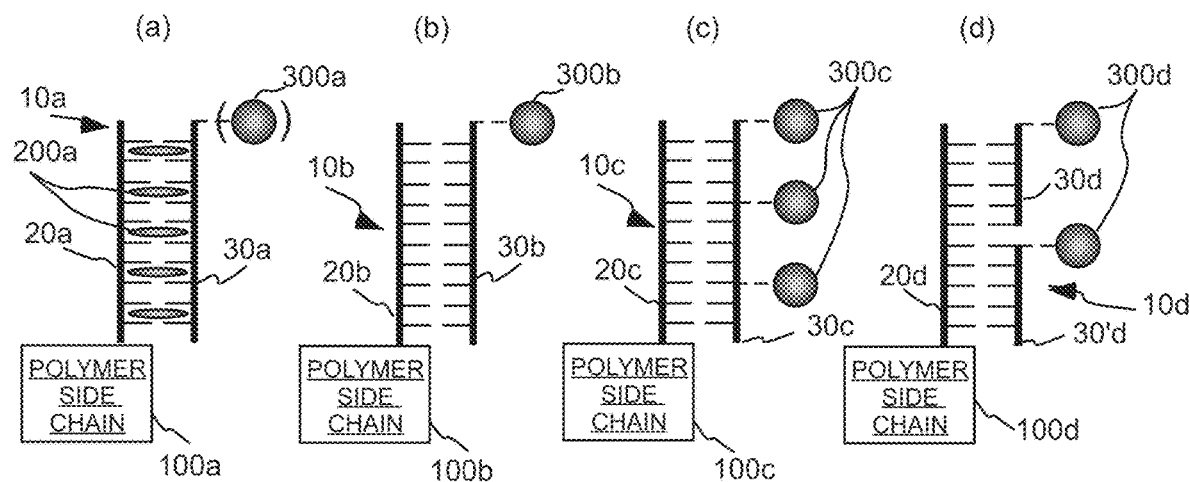
FIG. 7 illustrates schematically several alternative embodiments of fluorescent tags or labels hereof including double-stranded DNA or dnDNA attached to the side chain or branch of a polymer.

FIG. 7 illustrates schematically several alternative embodiments of fluorescent tags or labels hereof including double-stranded nucleic acid such as DNA attached to the side chain or branch of a polymer. Embodiment (a) of FIG. 7 is a schematic representation of the DNA bottlebrush polymer 10a discussed above. Once again, this embodiment includes two nucleic acid strands 20a and 30a. First strand 20a is covalently attached to each side chain 100a or bristle of, for example, a bottlebrush polymer, and second, complementary (either partially or fully complementary) strand 30a is associated or complexed therewith via hybridization. As used herein, the term "complementary" refers to either partially complementary or fully complementary strands of nucleic acid which may be complexed to form a duplex. Intercalating dyes 200a were bound noncovalently to the double stranded nucleic acid. Intercalated dye molecules 200a could generate fluorescence and/or transfer energy to an optional "acceptor" dye 300a attached covalently to one of strands 20a and 30a.

As discussed above, and as demonstrated by the covalent attachment of an acceptor dye such as Cy5 to one of the DNA strands (as, for example, discussed in connection with FIGS. 2A through 2F), fluorescent dye molecules can be covalently attached to one or both of the strands of nucleic acid. In the case that one or more florescent dye molecules are attached covalently to the nucleic acid duplex, the concern over dissociation of the dye molecules discussed above in connection with intercalated dye molecules is eliminated. As described above, brush polymers scaffolds were found facilitate retention of the intercalated dye molecules with dsDNA. Thus, brush polymers may be preferred for use with intercalated dyes. However, in the case of covalently attached dye molecules, polymers having multiple side chains that are not bottlebrush polymers may readily be used. Moreover, DNA often more readily allows intercalation of fluorescent dye molecules than other nucleic acids. In the case that all fluorescent dye molecule are covalently attached to the nucleic acid strands, other synthetic nucleic acids such as peptide nucleic acids (PNAs), gamma PNAs or locked nucleic acids (LNAs), which may not bind intercalator dyes with high affinity, may be used. In a number of embodiments, the length of the nucleic acid strands covalently attached to the extending side chains polymer scaffolds hereof is at least 6 mers. In a number of embodiments, the length of the side chains is in the range of 6 to 50 mers, or in the range of 6 to 40 mers. The length of the complementary nucleic acid strands complexed with the nucleic acid strand covalently attached to the polymer scaffolds hereof may, for example, also be at least 6 mers, in the range of 6 to 50 mers, or in the range of 6 to 40 mers. The two strands of the duplex need not be of the same length.

In the case of covalently bound fluorescent dye molecules or moieties, it is not necessary in some embodiments, to include a nucleic acid duplex in the compositions hereof. In that regard, one or more fluorescent dye molecules or moieties may be covalently bound to single strand of nucleic acid in the compositions hereof. Grafted polymers hereof, in which the grafting of many side chains is possible (either via grafting from or grafting onto a polymer core) may provide advantages in such embodiments. Moreover, the use of RDRP to synthesize such side groups provide significant control of polymer properties and/or inter-nucleic acid/nucleotide interaction. However, associating one or more fluorescent dye molecules attached to a strand of nucleic acid by complexing that strand to a complementary strand of nucleic acid attached to a polymeric scaffold hereof provide significant advantages in controlling the formation of the composition (including, for example, control of the association of different fluorescent dye molecules to the polymer scaffold). The presence of duplex strands also provided the capability of associating additional fluorescent dye molecules via intercalation as described above.

In embodiments (b), (c) and (d) of FIG. 7, the are no intercalated fluorescent dye molecules. In those embodiments, all fluorescent dye molecules are incorporated through covalent bonds to the nucleic acid strand termini and/or to one or more internal positions thereon. In embodiment (b), a single fluorescent dye molecule 300b is attached to strand 30b, which is complexed to a terminus of nucleic acid strand 20b. In embodiment (c), a plurality of fluorescent dye molecules 300c are attached to strand 30c (which is complexed to nucleic acid strand 20c) at the terminus of and internally to strand 30c. In embodiment (d), multiple short strands 30d and 30'd are complexed or hybridized to a single longer strand 20d as another way to introduce multiple dye molecules 300d per polymer side chain 100d.

Experimental Section

Synthesis of Azide Functionalized BBP [Poly(2-(2-Bromoisobutyryloxy)ethyl Methacrylate)-graft-Poly(2-(2-(2-Methoxyethoxy)ethoxy)ethyl Methacrylate) (PBiBEM-g-PMEO$_3$MA-N$_3$)] A poly [2-(2-bromoisobutyryloxy)ethyl methacrylate] (PBiBEM) macroinitiator with a degree of polymerization in the backbone of 400=m (Figure S10) was synthesized by following a previously reported procedure[1]. 2-(2-(2-methoxyethoxy)ethoxy)ethyl methacrylate) ($MEO_3MA$), used as monomer, was polymerized from PBiBEM macroinitiator by ATRP via a grafting-from method using Cu(I)Br, $Cu(II)Br_2$, and 4,4'-dinonyl-2,2'-dipyridyl(dNbpy). The initial ratio of reagents in the grafting-from reaction was [$MEO_3MA$]/[BiBEM]/[Cu(I)Br]/[Cu(II)$Br_2$]/[dNbpy]=500/1.0/0.9/0.1/2.0. $MEO_3MA$ (4.0 g, 17 mmol), PBiBEM (0.0096 g, 0.034 mmol of bromine initiating groups (BiBEM)), $Cu(II)Br_2$ (0.00077 g, 0.0034 mmol), dNbpy (0.028 g, 0.069 mmol), and 40% (v/v) anisole were added to a 25 mL Schlenk flask equipped with a stir bar. The mixture was degassed via three freeze-pump-thaw cycles, and then Cu(I)Br (0.0044 g, 0.031 mmol) was added when the solution was frozen during the final cycle. The flask was sealed and placed in an oil bath at 25° C. Conversion was analyzed by gas chromatography (GC) using anisole as the internal standard. The polymerization was stopped after 6 h and the flask was opened to air. The solution was passed through a column of neutral alumina, and then precipitated into hexanes three times. Finally the resulting polymer was dialyzed against three changes of THF for 2 days. The polymer was dried under vacuum at room temperature for 24 h providing PBiBEM400-g-$PMEO_3MA$180 with a degree of polymerization in the side chain of $MEO_3MA$=180 estimated by GC. A Schlenk flask was charged with PBiBEM400-g-$PMEO_3MA$180 (1.0 g, $0.088\times10^{-3}$ mmol), sodium azide (0.023 g, 0.35 mmol), and 10 mL DMF. The reaction mixture was stirred at room temperature for 48 h. The solution was dialyzed against four changes of DMF for 3 days to remove excess sodium azide, and then the DMF solvent in dialysis was replaced with THF. The solution was evaporated and dried under vacuum at room temperature for 24 h. The polymer was analyzed by $^1$H-NMR spectroscopy in $CDCl_3$, gel permeation chromatography (GPC) in THF, and FTIR spectroscopy providing PBiBEM400-g-$PMEO_3MA$180-$N_3$: $Mn=8.6\times10^6$, Mw/Mn=1.29, and 2110 $cm^{-1}$ (—N═N+═N—).

Oligonucleotides. DNA sequences with 5' terminal hexynyl and 5' Cy5 modifications were synthesized using solid phase oligonucleotide synthesis on a MerMade-4 synthesizer (Bio-automation, Plano, Tex., USA). Commercially available starting materials were used without further purification. Phosphoramidites (dA, dC, dG and T) with labile PAC protecting groups and appropriate reagents were purchased from ChemGenes (Wilmington, Mass. USA) and Glen Research (Sterling, Va. USA). Synthesis and de-protection of the oligonucleotides were conducted under standard protocols for PAC-protected amidites, as recommended by the manufacturers. The DNA synthesis columns were purchased from Biosearch Technologies, Inc (Novato, Calif. USA). 5'-amino-modified DNA and any unmodified DNA oligonucleotides were purchased from Integrated DNA Technologies, Inc. and obtained as lyophilized powders. The DNA sequences are illustrated in FIG. 1F in which underlining indicated the complementary regions.

Click Conjugation of Hexynyl-A to BBP-$N_3$. BBP-$N_3$ (4 mg) was dissolved in 100 μL of deionized (18.0 MΩ) $H_2O$ to give a 1 mM azide stock solution. A lyophilized powder of hexynyl-A was dissolved in $H_2O$ to obtain a 500 μM hexynyl stock solution. The BBP-$N_3$ (10 μL, 1 mM azide) and hexynyl-A (20 μL, 500 μM) solutions were mixed and degassed several times by blowing with argon, to remove any dissolved oxygen. Acetonitrile (1.5 μL, 20% ACN in $H_2O$ V/V) and a freshly prepared solution of sodium ascorbate prepared in deionized $H_2O$ (8 μL, 100 mM) were mixed and degassed in a separate vial. The two solutions were added to 4.5 μL of degassed deionized $H_2O$ and the final pH and salt concentration were brought to pH=7.5 and 100 mM Na with 5 μL of 10× PBS buffer. The solution was mixed thoroughly and degassed. A degassed solution of $CuSO_4$ (1 μL, 100 mM) was added to initiate the reaction and was allowed to run for 3 hours at room temperature with gentle shaking. The DBBP product was purified with a 30 kDa molecular weight cutoff filter (Millipore) and dissolved in PBS buffer (pH=7.5, =100 mM). The DNA concentration was calculated using the UV absorbance at 260 nm using a NanoDrop UV/Vis spectrometer. The final DBBP product was stored in a −14° C. freezer to be used later. For solution phase FTIR experiments the isolated DBBP from the molecular weight cutoff filter was dissolved in deionized water instead of PBS buffer.

Synthesis of A-BBP with 40% Saturation of Azide Terminating Side Chains. The general procedure for the conjugation of hexynyl-DNA to BBP-$N_3$ described above was followed by using 40% as much hexynyl-A DNA (8 μL, 500 μM stock).

Synthesis of PEO/A-BBP with 40% Hexynyl-A and 60% PEO-alkyne by Sequential Click Conjugation. An alkyne-terminated poly(ethylene oxide)(PEO-alkyne) synthesized using a previously reported procedure[2] was used for the click reaction. PEO-alkyne (2.08 mg) was dissolved in 5 mL of deionized water to make a 200 μM stock of alkyne. Azide from BBP-$N_3$ (10 μL, 1 mM) and hexynyl-A (8 μL, 500 μM) were mixed and degassed several times to remove any dissolved oxygen. Acetonitrile (1.5 μL, 20% ACN in $H_2O$ V/V) and a freshly prepared solution of sodium ascorbate prepared in deionized $H_2O$ (8 μL, 100 mM) were mixed and degassed in a separate vial. The two solutions were added to 1.5 μL of degassed deionized $H_2O$ and the final pH and salt concentration were brought to pH=7.5 and 100 mM $Na^+$ with 5 μL of 10× PBS buffer. The solution was mixed thoroughly and degassed. A degassed solution of $CuSO_4$ (1 μL, 100 mM) was added to initiate the reaction and was allowed to run for 1 hour at room temperature with gentle shaking. After 1 hour a degassed solution of PEO-alkyne (15 μL, 200 μM) was added and the reaction was allowed to run for two more hours. The DBBP product was purified using molecular weight cutoff filters.

Synthesis of A/B-BBP with 99.5% Hexynyl-A and 0.5% Hexynyl-B. The sequential click conjugation method illustrated in FIG. 4A was followed using BBP-$N_3$ (10 μL, 1 mM azide), hexynyl-B (5 μL, 10 μM) and hexynyl-A (19.9 μL, 500 μM).

Hybridization of DNA Duplexes and YOYO-1 Intercalation. An equimolar mixture of Seq.A from DBBP and Cy5-Acomp were mixed together in buffered aqueous solution (PBS buffer, pH=7.5, 100 mM Nat) to give a 100 nM final concentration of duplex DNA. Nonbrush DNA duplexes were prepared by mixing seq. A and Cy5-Acomp in an equimolar ratio in buffered solution to give the same final concentration of duplex DNA. The same step was followed to prepare bush and nonbrush duplex DNA without Cy5 dye by using $A_{comp}$ in place of Cy5-$A_{comp}$. The vials were incubated in 90° C. water bath for 2 minutes and quickly transferred to a water bath at 65° C. After incubating for 15 minutes at 65° C. the samples are cooled down to 25° C. within a period of 1 hour. The DBBP samples with 40% loading of seq. A were mixed with equimolar ratio of Cy5-$A_{comp}$ and $A_{comp}$ separately in buffered solutions to give double stranded DBBPs with low loading of DNA.

Preparation of Antibody-DNA Conjugates. Antibody-DNA conjugation (see, for example, FIG. 5A-5C) was performed using the Solulink protein-oligo conjugation kit (catalog S-9011-1, Solulink) which uses bisaryl hydrazone conjugation chemistry. Antibody and DNA modification reactions were optimized to obtain a single DNA strand conjugated per antibody. Prior to functionalization, affinity-purified, unlabeled goat-antimouse IgG antibody (Jackson Immunoresearch) was desalted using MicroSpin G-50 columns (GE Healthcare) and buffer exchanged (modification buffer, 100 mM phosphate, 150 mM NaCl, pH 8) using molecular weight cutoff filters (50 kDa, Millipore Corporation) to bring the final protein concentration to 2.9 mg/mL. 1.1 mg of SANH (succinimidyl 6-hydrazinonicotinamide acetone hydrazine) reagent provided in the kit was dissolved in 150 µL of N,N-dimethylformamide (DMF). The SANH solution and the desalted, buffer-exchanged antibody was mixed in a 5:1 (SANH:antibody) molar ratio. Separately 1.7 mg of Hydralink SFB (Succinimidyl 4-formylbenzoate) reagent provided in the kit was dissolved in 80 µL of DMF. 5'-aminated DNA (NH2-B', Integrated DNA Technologies, Inc.) was dissolved in modification buffer to make a 1 mM stock solution. The SFB reagent and the NH$_2$—B' was mixed in a 5:1 (SFB:DNA) molar ratio. Both antibody and DNA coupling reactions were performed at room temperature for 2 hours on a gently rotating shaker. Excess SANH and SFB were removed using MicroSpin G-50 and G-25 columns, respectively. The modified antibody and the DNA were dissolved in conjugation buffer (100 mM phosphate, 150 mM NaCl, pH 6). Molar substitution ratio (MSR) assays were performed using the standard protocols provided by the vendor to determine the number of modifications per antibody and DNA strand. SFB-derivatized DNA was then combined with the SANH-derivatized antibody in 1:5 ratio and allowed to react overnight at room temperature on a gently rotating shaker. Unreacted DNA was removed using 50 kDa filters. Fractions from each filtration round were tested for presence of unbound free DNA ($A_{260}$ using NanoDrop spectrophotometer). The conjugation of antibody-DNA was verified spectrophotometrically, by the presence of the bisaryl hydrazone linkage ($\lambda_{max}$=354 nm) formed between SANH and SFB.

Figure 6:
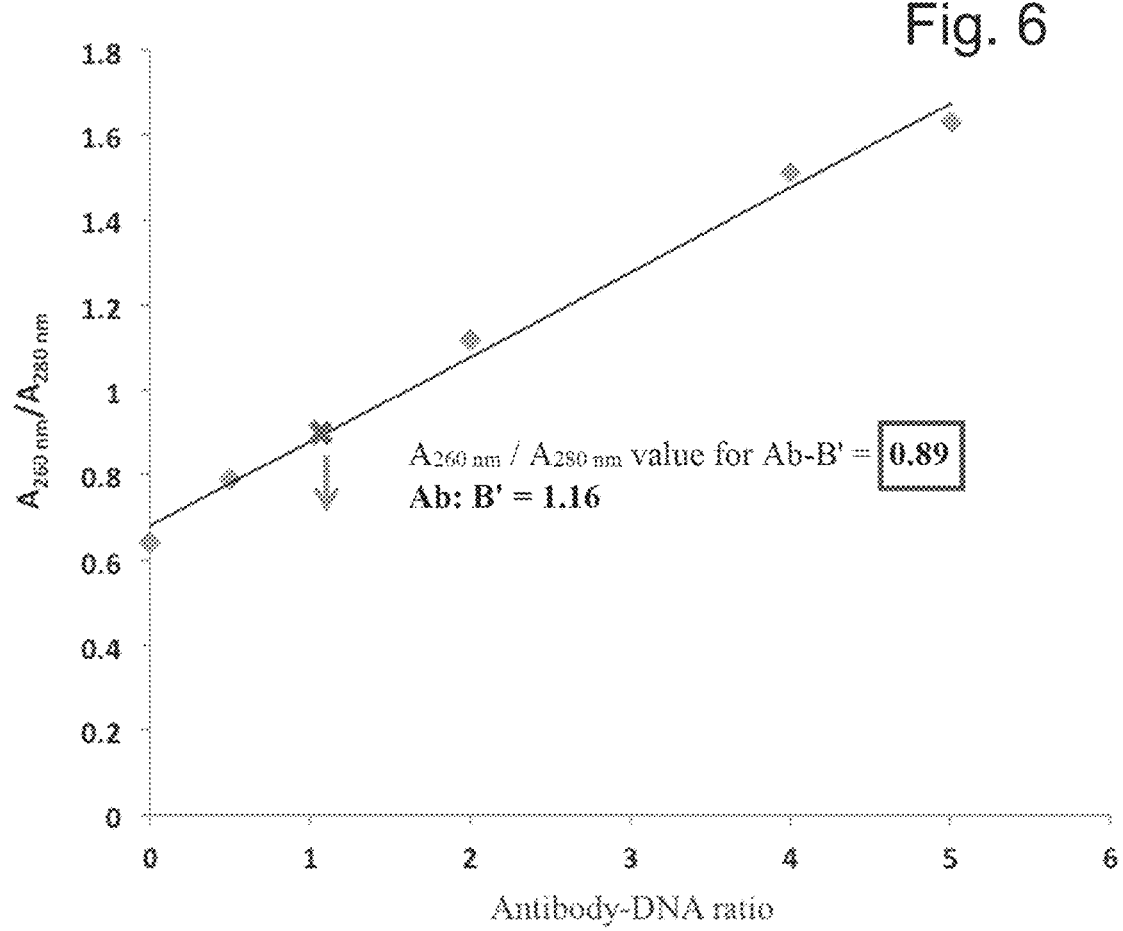
FIG. 6 illustrates a calibration plot of $A_{260\ nm}/A_{280\ nm}$ vs. antibody-DNA ratio to calculate the number of DNA strands attached per antibody.

Determination of Antibody:DNA Ratio. To quantitatively determine the number of DNA strands conjugated per antibody, a calibration experiment was conducted. 20 µL solutions with various ratios of antibody to DNA were mixed as follows: 1:0 (4 µM and 0 µM, respectively), 1:0.5 (4 µM and 2 µM, respectively), 1:2 (4 and 8 µM, respectively), 1:4 (4 and 16 µM, respectively), and 1:5 (4 and 20 µM, respectively). Using the NanoDrop spectrophotometer, the $A_{260\ nm}/A_{280\ nm}$ absorbance ratios were determined and recorded for each solution. The obtained calibration curve was then used to determine the number of DNA strands per antibody (FIG. 6). This procedure accounts for the fact that the absorbance of the DNA (260 nm) overlaps with the absorbance of the antibody (280 nm). For the Ab-B' conjugates reported here, an average of one DNA strand was attached per antibody.

Antibody-DBBP Hybridization DBBP with Seq. B: Seq A in a 1:199 ratio was first hybridized with Cy5-Acomp by mixing equimolar amount of Cy5-Acomp and Seq. A on DBBP in PBS buffer (100 mM Nat, pH 7.5) and annealing. The resulting DBBP should have, on average, one unhybridized Seq.B strand available for hybridization to the antibody functionalized with its complement (Ab-B'). Antibody and DBBP (10 µM each final concentration) were mixed and allowed to hybridize at 25° C. overnight on a gently rotating shaker. The antibody-conjugated DBBP (10 µM) was stored at 4° C. until further use.

Labeling and Detection of c-myc Targets of Yeast Cells with Antibody-DBBP Nanotag. Yeast cells expressing c-myc-tagged scFv ($10^7$ cells) were suspended in calcium- and magnesium-free PBS wash buffer (pH=7.5, Na$^+$=100 mM, 1 µg/mL PLURONIC® F-127, a non-ionic surfactant polyol available from Thermo Fisher Scientific). The cells were incubated with 0.5 µM final concentration of anti-c-myc mouse antibody for half an hour at 4° C., washed three times with 500 µL of wash buffer, and resuspended in 500 µL of the same buffer. The cells were incubated with 50 nM final concentration of goat anti-mouse antibody-DBBP complex for 30 minutes at 4° C. The cells were washed three times with 500 µL wash buffer. YOYO-1 was added to give a 50 µM final concentration in a total volume of 500 µL PBS buffer (pH=7.5, Na$^+$=100 mM, 1 µg/mL PLURONIC® F-127). Similarly, 50 nM final concentrations of Alexa 647-tagged goat anti-mouse IgG (H+L) (Thermo Fisher Scientific) and Qdot® 655 tagged goat anti-mouse IgG (H+L) (Thermo Fisher Scientific) were separately used as controls. Labeled cells were analyzed by fluorescence activated cell sorting (FACS) using a Coulter Epix Elite flow cytometer (Beckman-Coulter, Fullerton, Calif.). The following dichroic lenses (DL)/band-pass (BP) filters were used: 550DL/530BP for YOYO-1-donor fluorescence channel, and 720DL/695 BP for Cy5-acceptor fluorescence channel. Further, a Carl Zeiss LSM 510 Meta DuoScan Inverted Spectral Confocal Microscope was used for fluorescence imaging analysis at 100× objective magnification. Yeast cell samples were prepared according to the yeast cell fluorescent staining protocol outlined above, except the final volume of each sample was 60 µL of PBS wash buffer (pH=7.5, Na$^+$=100 mM, 1 µg/mL PLURONIC® F-127). 20 µL of the cell suspension was placed on a 35 mm glass bottom micro well dish (Mattek, part no. P35G-1.5-14-C). The micro well plates for yeast cells were treated with concanavalin A. Enough wash buffer was added to fill the micro well before viewing under the microscope. The pin hole opening was set to the minimum setting and the tube current was set to 0.6 A for imaging. Raw images were collected using ZEN 2009 software without applying any digital enhancements.

Labeling and Detection of Biotin Targets on Polystyrene Beads by Antibody-DBBP Nanotag. Biotin-coated polystyrene beads ($10^6$ beads) were suspended in 60 µL total volume of calcium- and magnesium-free PBS (pH=7.5, Na$^+$=100 mM, 0.02% Triton X-100) buffer. The beads were incubated with 0.5 µM final concentration of anti-biotin mouse IgG(H+L) (Jackson Immunoresearch) for half an hour at 25° C., washed three times with 500 µL of wash buffer, and resuspended in 500 µL of the same buffer. The beads were incubated with 50 nM final concentration of goat anti-mouse antibody-DBBP complex for 30 minutes at 25° C. The beads were washed three times with 500 µL wash buffer. YOYO-1 was added to give a 50 µM final concentration in a total volume of 500 µL PBS buffer (pH=7.5, Na$^+$=100 mM, 1 µg/mL Triton X-100). Similarly, 50 nM final concentrations of Alexa 647-tagged goat anti-mouse IgG (H+L) (Thermo Fisher Scientific) and Qdot® 655 tagged goat anti-mouse IgG (H+L) (Thermo Fisher Scientific) were separately used as controls. Samples were allowed to incubate for 30 minutes at 25° C. and washed with 150 µL PBS. Samples were resuspended in 500 µL PBS. Labeled beads were analyzed by fluorescence activated cell sorting (FACS) using a Coulter Epix Elite flow cytometer (Beckman-Coulter, Fullerton, Calif.). The following dichroic lenses (DL)/band-pass (BP) filters were used: 550DL/530BP for YOYO-1 donor fluorescence channel, and 720DL/695 BP for Cy5 acceptor fluorescence channel. Further, a Carl Zeiss LSM 510 Meta DuoScan Inverted Spectral Confocal Microscope was used for fluorescence imaging analysis at 100× objective magnification. Bead samples were prepared according to the microbead fluorescent staining protocol outlined above, except the final volume of each sample was 60 μL of PBS wash buffer (pH=7.5, $Na^+$=100 mM, 1 μg/mL Triton X-100). 20 μL of the bead suspension was placed on a 35 mm glass bottom microwell dish (Mattek, part no. P35G-1.5-14-C). Enough wash buffer was added to fill the microwell before viewing under the microscope. The pin hole opening was set to the minimum setting and the tube current was set to 0.6 A for imaging. Raw images were collected using ZEN 2009 software without applying any digital enhancements.

Dot Blot Experiments. Maltose-binding protein was blotted on a pure nitrocellulose transfer and immobilization paper (pore size 0.45 μm, Perkin Elmer) in increasing amounts. (spots of 0.5 ng to 25 ng in duplicate to get two rows) and was allowed to dry for 30 mins at 25° C. Non-specific binding was inhibited with blocking buffer (5% milk) for 1 hour at 25° C. The 5% milk was prepared in Tris-buffered saline and Tween (TBST) buffer (pH=8.5). The membrane was washed three times using the TBST buffer to get rid of any unbound protein and excess milk. 1 μL of the anti-MBP monoclonal antibody-HRP conjugate (New England Biolabs) was added to 1 mL of 5% milk (1:1000 dilution) and the membrane was allowed to be covered in this solution containing the primary antibody overnight at 4° C. with gentle shaking. The membrane was washed in 25 mL TBST for 5 minutes with gentle shaking, 3 times for 2 minutes each. A 1:1000 dilution was made with goat anti-mouse IgG-Alexa 647 conjugate or the goat anti-mouse IgG-DBBP-nanotag with 1 ml TBST to get similar concentrations of the secondary antibody (final concentration=2 μg/mL=ca. 10 nM). The membrane was incubated in the solution for 3 hours. The washing steps were performed in triplicate with TBST and TBS buffers. The membrane was dried and was imaged using the Typhoon FLA 9000 scanner. YOYO-1 was excited using the excitation wavelength at 473 nm at 250 V and the direct excitation of Cy5 and Alexa 647 was performed at 650 nm at 250 V. The blots were scanned to get the emission at 695 nm.

Fluorescence measurements. Fluorescence measurements were taken in 0.1 μM final concentrations of duplex DNA. YOYO-1 (available from Thermo Fisher Scientific). YOYO-1 was added in 0.5 μM final concentration to the pre-annealed DNA duplexes and mixed for one minute before taking fluorescence measurements. Energy transfer signals were monitored by exciting the donor YOYO-1 at 450 nm and the resulting emission of Cy5 was measured at 670 nm. The band passes for both excitation and emission monochromators were 5 nm. The Energy Transfer efficiency (ET) was calculated on the basis of the fluorescence intensity of the donor in the presence (FDA) and absence (FD) of the acceptor dye based to the following equation: $ET=1-(F_{DA}/F_D)$.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A composition comprising: a polymer comprising a plurality of side chains, one of a plurality of a first strand of nucleic acid being attached to each of the plurality of the side chains, one of a plurality of a second strand of nucleic acid which is complementary to the first strand of nucleic acid being complexed to each of the plurality of the first strand of nucleic acid to form a double-stranded nucleic acid on each of the plurality of the side chains, a plurality of at least one fluorescent compound being intercalated into the double-stranded nucleic acid on each of the plurality of the side chains, the double-stranded nucleic acid further comprising at least one other fluorescent compound different from the at least one fluorescent compound to which excitation energy can be transferred to effect a red shift in an emission wavelength, and a moiety being attached to one of the side chains, wherein the moiety has a binding affinity for one or more target species, wherein the polymer is a bottle-brush copolymer comprising a backbone from which the side chains extend, the side chains being formed via a reversible-deactivation radical polymerization and wherein the composition is mobile in a liquid matrix.

2. The composition of claim 1 wherein the one of the side chains to which the moiety is attached comprises a third strand of nucleic acid, the moiety being attached to a fourth strand of nucleic acid which is complementary to the third strand of nucleic acid, the fourth strand of nucleic acid being complexed to the third strand of nucleic acid.

3. The composition of claim 1 wherein the moiety is an antibody.

4. The composition of claim 1 wherein the at least one other fluorescent compound is covalently attached to the second strand of nucleic acid.

5. The composition of claim 1 wherein the reversible-deactivation radical polymerization is atom transfer radical polymerization.

6. The composition of claim 1 wherein the first strand of nucleic acid is a first strand of DNA and the second strand of nucleic acid is a second strand of DNA.

7. A composition comprising: a polymer comprising a plurality of side chains, one of a plurality of a first strand of nucleic acid being attached to each of the plurality of the side chains, one of a plurality of a second strand of nucleic acid which is complementary to a first portion the first strand of nucleic acid being complexed to each of the plurality of the first strand of nucleic acid to form a double-stranded nucleic acid on each of the plurality of the side chains, a plurality of at least one fluorescent compound being covalently attached to the second strand of the double-stranded nucleic acid on each of the plurality of the side chains, a third strand of nucleic acid which is complementary to a second portion of the first strand of nucleic acid and is complexed to the second portion of the first strand of nucleic acid, the third strand of nucleic acid having one or more of the at least one fluorescent compound covalently attached thereto, and a moiety being attached to one of the side chains, wherein the moiety has a binding affinity for one or more target species and wherein the composition is mobile in a liquid matrix.

8. The composition of claim 7 wherein the polymer is a bottlebrush copolymer comprising a backbone from which the side chains extend, the side chains being formed via a reversible deactivation radical polymerization.

9. A method of labeling a target species, comprising: attaching a label to the target species, wherein the label comprises a composition comprising a polymer comprising a plurality of side chains, one of a plurality of a first strand of nucleic acid being attached to each of the plurality of the side chains, one of a plurality of a second strand of nucleic acid which is complementary to the first strand of nucleic acid being complexed to each of the plurality of the first strand of nucleic acid to form a double-stranded nucleic acid on each of the plurality of the side chains, a plurality of at least one fluorescent compound being attached to the second strand of the double-stranded nucleic acid on each of the plurality of the side chains, the double-stranded nucleic acid further comprising at least one other fluorescent compound different from the at least one fluorescent compound to which excitation energy can be transferred to effect a red shift in an emission wavelength, and a moiety being attached to one of the side chains, wherein the moiety has a binding affinity for the target species, wherein the polymer is a bottlebrush copolymer comprising a backbone from which the side chains extend, the side chains being formed via a reversible-deactivation radical polymerization and wherein the composition is mobile in a liquid matrix.

10. The method of claim 9 wherein the one of the side chains to which the moiety is attached comprises a third strand of nucleic acid, the moiety being attached to a fourth strand of nucleic acid which is complementary to the third strand of nucleic acid, the fourth strand of nucleic acid being complexed to the third strand of nucleic acid.

11. The method of claim 10 wherein the moiety is an antibody.

12. The method of claim 11 wherein the antibody is a secondary antibody.

13. The method of claim 12 wherein the secondary antibody has affinity for a primary antibody, and the primary antibody has affinity for the target species.

14. The method of claim 9 wherein the at least one other fluorescent compound is covalently attached to the second strand of nucleic acid.

15. The method of claim 9 wherein the reversible-deactivation radical polymerization is atom transfer radical polymerization.

16. A method of labeling a target species, comprising: attaching a label to the target species, wherein the label comprises a composition comprising a polymer comprising a plurality of side chains, one of a plurality of a first strand of nucleic acid being attached to each of the plurality of the side chains, one of a plurality of a second strand of nucleic acid which is complementary to a first portion of the first strand of nucleic acid being complexed to each of the plurality of the first strand of nucleic acid to form a double-stranded nucleic acid on each of the plurality of the side chains, a plurality of at least one fluorescent compound being covalently attached to the second strand of the double-stranded nucleic acid on each of the plurality of the side chains, a third strand of nucleic acid which is complementary to a second portion of the first strand of nucleic acid and is complexed to the second portion of the first strand of nucleic acid, the third strand of nucleic acid having one or more of the at least one fluorescent compound covalently attached thereto, and a moiety being attached to one of the side chains, wherein the moiety has a binding affinity for the target species and wherein the composition is mobile in a liquid matrix.

17. The method of claim 16 wherein the polymer is a bottlebrush copolymer comprising a backbone from which the side chains extend, the side chains being formed via a reversible-deactivation radical polymerization.

18. The method of claim 16 wherein the first strand of nucleic acid is a strand of first strand of DNA and the second strand of nucleic acid is a second strand of DNA.

* * * * *